(12) United States Patent
Hatanaka et al.

(10) Patent No.: US 6,599,713 B1
(45) Date of Patent: Jul. 29, 2003

(54) METHOD FOR QUANTITATING LEUKOCYTE COUNT IN WHOLE BLOOD SAMPLE

(75) Inventors: Yoshihiro Hatanaka, Shizuoka-ken (JP); Ryo Serizawa, Shizuoka-ken (JP)

(73) Assignee: Asahi Kasei Kabushiki Kaisha, Osaka (JP)

( * ) Notice: Subject to any disclaimer, the term of this patent is extended or adjusted under 35 U.S.C. 154(b) by 0 days.

(21) Appl. No.: 09/913,161

(22) PCT Filed: Mar. 29, 2000

(86) PCT No.: PCT/JP00/01958

§ 371 (c)(1),
(2), (4) Date: Aug. 10, 2001

(87) PCT Pub. No.: WO00/58726

PCT Pub. Date: Oct. 5, 2000

(30) Foreign Application Priority Data

Mar. 29, 1999 (JP) ............................................. 11/086100

(51) Int. Cl.$^7$ ................................................ C12Q 1/28
(52) U.S. Cl. ......................................................... 435/28
(58) Field of Search ........................................... 435/28

(56) References Cited

U.S. PATENT DOCUMENTS 5,639,630 A    6/1997  Malin et al.

FOREIGN PATENT DOCUMENTS

| JP | 8-145993 | 6/1996 |
|---|---|---|
| JP | 8-308593 | 11/1996 |
| JP | 9-72906 | 3/1997 |
| JP | 9-121893 | 5/1997 |
| JP | 9-196919 | 7/1997 |
| JP | 11-32793 | 2/1999 |
| WO | 91/04491 | 4/1991 |
| WO | 92/14136 | 8/1992 |
| WO | 92/14147 | 8/1992 |
| WO | 92/16826 | 10/1992 |
| WO | 93/01306 | 1/1993 |
| WO | 94/03774 | 2/1994 |
| WO | 99/46599 | 9/1999 |

OTHER PUBLICATIONS

Yamao et al., "Automated Blood Cell Count and C–reactive Protein Measuring Instruments: LC–270," *READOUT*, 16, HORIBA Technical Reports, 1998, pp. 11–15.

Bradley, M.D. et al., "Measurement of Cutaneous Inflammation: Estimation of Neutrophil Content with an Enzyme Marker," *The Journal of Investigative Dermatology*, V. 78, 1982, pp. 206–209.

Cramer et al., "A Simple Reliable Assay for Myeloperoxidase Activity in Mixed Neutrophil–Eosinophil Cell Suspensions: Application to Detection of Myeloperoxidase Deficiency," *Journal of Immunological Methods*, V. 70, 1984, pp. 119–125.

W. M. Kuebler et al., "Measurement of Neutrophil Content in Brain and Lung Tissue by a Modified Myeloperoxidase Assay," *International Journal of Microcirculation*, V. 16, 1996, pp. 89–97.

Goto et al., "Rinsho Kensa (Clinical Examinations)," V. 40, 1969, pp. 859–863.

Ihi et al., "Elevated Concentrations of Human Neutrophil Peptides in Plasma, Blood, and Body Fluids from Patients with Infections," *Clinical Infectious Diseases*, V. 25, 1997, pp. 1134–1140.

Borregaard et al., "Granules of the Human Neutrophilic Polymorphonuclear Leukocyte," *Blood*, V. 89, No. 10, May 15, 1997, pp. 3503–3521.

"Sin–ban Kaimen–Kassei–Zai Handobukku (New Edition, Surfactant Handbook)," edited by Tokiyuki Yoshida et al., Kogaku Tosho Co., Japan, 1987, pp. 234–245.

*Handbook of Industrial Surfactants*, Second Edition, edited by Michael and Irene Ash, Gower Publishing Limited, 1997, pp. v–vii.

Yamagishi et al., "Rinsho Byori (Clinical Pathology)," V. 32, 1984, pp. 1389–1394.

Nishida, "Kitasato Igaku (Kitasato Medicine)," V. 16, 1986, pp. 393–401.

Shimetani, "Kitasato Igaku (Kitasato Medicine)," V. 24, 1994, pp. 97–103.

"How to Read and Consider Clinical Examination Data in a Clinically Useful Manner," compiled under the supervision of Kin–ya Kawano et al., Sogo–Igakusha Co., Japan, 1997, p. 236.

Covalciuc et al., "Comparison of Four Clinical Specimen Types for Detection of Influenza A and B Viruses by Optical Immunoassay (FLU OIA Test) and Cell Culture Methods," *Journal of Clinical Microbiology*, V. 37, No. 12, Dec. 1999, pp. 3971–3974.

*Primary Examiner*—Sandra E. Saucier
(74) *Attorney, Agent, or Firm*—Young & Thompson

(57) ABSTRACT

Disclosed is a method for determining a white blood cell count of a whole blood sample, which comprises: mixing a whole blood sample with a surfactant to thereby obtain a mixture; allowing the mixture to stand for a time sufficient to lyze the white blood cells contained in the whole blood sample and release intrinsic myeloperoxidase from the white blood cells; measuring the concentration of the released myeloperoxidase in the mixture; and determining the white blood cell count in the whole blood sample, based on the concentration of the released myeloperoxidase. Also disclosed is a method of the present invention, in which, in addition to a white blood cell count of a whole blood sample, the concentration of C-reactive protein contained in the same whole blood sample is measured.

15 Claims, 8 Drawing Sheets

METHOD FOR QUANTITATING LEUKOCYTE COUNT IN WHOLE BLOOD SAMPLE

BACKGROUND OF THE INVENTION

1. Field of the Invention

The present invention relates to a method for determining a white blood cell count of a whole blood sample. More particularly, the present invention is concerned with a method for determining a white blood cell count of a whole blood sample, which comprises: mixing a whole blood sample with a surfactant to thereby obtain a mixture; allowing the mixture to stand for a time sufficient to lyze the white blood cells contained in the whole blood sample and release intrinsic myeloperoxidase from the white blood cells; measuring the concentration of the released myeloperoxidase in the mixture; and determining the white blood cell count in the whole blood sample, based on the, concentration of the released myeloperoxidase. By the method of the present invention for determining a white blood cell count, the determination of a white blood cell count and/or a neutrophil count of a whole blood sample can be performed easily and rapidly without the need to separate blood cells from the whole blood sample. Further, by the determination method of the present invention, in addition to a white blood cell count of a whole blood sample, the concentration of C-reactive protein contained in the same whole blood sample can be measured, so that the presence or absence of an infectious disease and the graveness of an inflammation can be diagnosed rapidly and easily and at low cost.

2. Prior Art

In recent years, in the initial steps of diagnosis of patients, as examination items for judging whether or not patients have a bacterial infectious disease, the white blood cell count of a whole blood sample and the concentration of C-reactive protein (hereinafter, frequently referred to simply as "CRP") contained in a whole blood sample are determined. In this connection, for enabling doctors to take adequate measures, such as the administration of an antibiotic, it has been desired to develop determination techniques which can produce results rapidly and easily and at low cost.

Usually, the determination of the white blood cell count is performed using a commercially available automated blood cell counting apparatus which is based on the aperture-impedance method, wherein the apparatus is represented by COULTER COUNTER™ (manufactured and sold by COULTER ELECTRONICS, INC., the U.S.A.). However, the concentration of CRP, which is a plasma protein, cannot be determined by such an apparatus.

Recently, there has been put into the market an apparatus for determining both the white blood cell count and the CRP concentration, which apparatus is described in Yasuo YAMAO, Hiroshi OKUNARI and Henri CHAMPEIX: Readout, 16, 11–15 (1998), wherein, in the apparatus, a blood cell counting apparatus based on the aperture-impedance method is given a CRP determination function based on a latex turbidimetric immunoassay. In the case of the use of such apparatus, the procedure is as follows: the red blood cells in the whole blood sample are first lyzed, and, then, the white blood cell count is determined by the aperture-impedance method, and, subsequently, the CRP determination is performed by a method in which the blood sample containing the lyzed blood cells is reacted with latex beads having bound thereto an anti-CRP antibody for a predetermined time, and then the CRP concentration is determined by a latex turbidimetric immunoassay. That is, in the case of the use of the above-mentioned apparatus, the determination of the white blood cell count and the determination of the CRP concentration are performed based on different principles, so that completely different operations are necessary for the determination. Therefore, the conventional method using the above-mentioned apparatus has drawbacks in that very cumbersome operations are necessary and that a number of reagents are used for the determination, thus leading to an increase in cost. In addition, the maintenance of the apparatus needs much time and large cost. Due to these drawbacks, an automated blood cell counting apparatus has not yet been introduced in almost all of medical institutions which have the responsibility of providing primary care, such as practicing physicians, and general hospitals, and therefore, the needs for medical care cannot be fully satisfied.

As a means to solve the above-mentioned problems, conceivable is a method in which both the white blood cell count and the CRP concentration are determined, based on the same principle. Specifically, conceivable is a method in which, with respect to a single sample of whole blood, both the white blood cell count and the CRP concentration are determined by an immunological method. An immunological determination of the white blood cell count can be made by measuring a protein which is specifically present in white blood cells.

It is generally know that, when a bacterial infection or an inflammation occurs, the number of neutrophis in the blood is increased, wherein the neutrophis have a largest proportion among all types of white blood cells. Therefore, by determining the neutrophil count, the increase and decrease in the number of white blood cells can be detected, so that the presence or absence of a bacterial infectious disease and the graveness of an inflammation can be judged.

As an example of a method for measuring the neutrophil count of an inflamed site of tissue or measuring the white blood cell count or the granulocyte count of a whole blood sample, there can be mentioned the method described in Peter P. Bradley, Dennis A. Priebat, Robert D. Christensen and Gerald Rothstein: *J. Invest. Dermatol.*, 78, 206–209 (1982). This method is as follows. First, neutrophils are separated from a whole blood sample by using the Ficoll reagent, or an inflamed skin tissue is obtained. The obtained neutrophils or the obtained inflamed skin tissue is homogenized in a 50 mM potassium phosphate buffer solution (pH 6.0) containing 0.5% hexadecyltrimethylammonium bromide (HTAB) and then sonicated to extract myeloperoxidase, and subsequently the enzyme activity of the extracted myeloperoxidase is determined.

Another method is disclosed in Rita Cramer, Maria Rosa Soranzo, Pietro Dri, Renzo Menegazzi, Anna Pitotti, Giuliano Zabucchi and Pierluigi Patriarca: *Journal of immunological Methods*, 70, 119–125 (1984). This method is as follows. Dextran (MW 200,000) is added to blood containing a solution of ACD (acid citrate dextrose) as an anticoagulant, to obtain a mixture. From the obtained mixture, red blood cells are removed. Subsequently, the Ficoll reagent is added to the resultant, and granulocytes are separated from the resultant mixture by centrifugation. Then, $2 \times 10^4$ cells of the granulocytes are mixed with a 0.1 M phosphate buffer solution (pH 7.0) containing 13 mM guaiacol and 0.02% cetyltrimethylammonium bromide. 1 $\mu$mol of $H_2O_2$ is added thereto, and the peroxidase activity is measured.

W. M. Kuebler, C. Atels, L. Schuerer and A. E. Goetz: Int. *J. Microcirc.*, 16, 89–97(1996) disclose the following method. Polymorphonuclear white blood cells are separated from whole blood by using the Ficoll reagent. The obtained white blood cells are lyzed with a 50 mM potassium phosphate buffer solution (pH 6.0) containing 0.5% HTAB, and then the enzyme activity of the myeloperoxidase in the resultant cell lysis mixture is determined. Further, the above-mentioned prior art document also discloses a method in which rat brain tissue or rabbit lung tissue is homogenized in 1 ml of a 0.02 M potassium phosphate buffer solution (pH 7.4) which is cooled with ice, and then 1 ml of 0.02 M potassium phosphate buffer solution (pH 7.4) is added thereto, and the resultant is centrifuged at 2,000 rpm for 15 minutes at 4° C. to obtain a centrifugation product containing a supernatant. Subsequently, the enzyme activity of the myeloperoxidase in the supernatant is determined. Further, the residue of the centrifugation product is incubated at 60° C. for 2 hours, and then homogenized with a 50 mM potassium phosphate buffer solution (pH 6.0) containing 0.5% HTAB, and then sonicated, and the resultant is centrifuged at 20,000 rpm for 15 minutes at 4° C. to obtain a supernatant. Subsequently, the enzyme activity of the myeloperoxidase in the supernatant is determined.

International application publication No. WO93/01306 discloses the following method. A predetermined amount of blood is put on a glass microfiber filter set in a syringe. Water is added to the blood, and the red blood cells are lyzed without breaking the granulocytes, and the cell lysis components in the blood are removed by pressure washing, to thereby remove components hindering the determination of the granulocyte count and obtain non-lyzed granulocytes carried on the glass microfiber filter. The glass microfiber filter carrying the non-lyzed granulocytes is dried, and a 50 mM phosphate buffer solution containing 0.005% Triton™ X-100, 30 mM 3-amino-1,2,4 triazole, 0.0005% $H_2O_2$ and 0.5 mg/ml o-tolidine is dropped on the glass microfiber filter, so that myeloperoxidase is released from the granulocytes and forms blue spots by staining. The blue spots are counted as representing the granulocytes.

Japanese Patent Application Laid-Open Specification No. 8-308593 (corresponding to EP 743519 and U.S. Pat. No. 5,639,630) discloses the following method. A solution is prepared which comprises: a nonionic polyethoxylate surfactant, an anionic surfactant or an amphoteric surfactant in a concentration which lyzes the red blood cells in whole blood thereby releasing hemoglobin from the red blood cells but which does not break the white blood cells; formaldehyde or paraformaldehyde in a concentration which chemically crosslinks the white blood cells but which does not crosslink the red blood cells; a sugar or a sugar alcohol which enhances the detectablility of the lymphocytes; and a buffer solution which causes the reaction mixture to have a pH value which is at or around the neutral point, specifically a pH range of from about 6.8 to about 8.0. The solution is mixed with whole blood, and the resultant mixture is heated to about 60 to 75° C. to lyze the red blood cells and cross-link the white blood cells. A part of the white blood cells are stained using the intrinsic peroxidase activity, and cell counts of the different types of white blood cells are determined by electro-optical analysis using absorbance or light scattering.

However, these methods have problems as follows. Since myeloperoxidase is substantially released from neutrophils present in the tissues of the skin, the brain and the lung, and subjected to the determination of the enzyme activity, it is necessary to conduct extremely cumbersome operations, such as homogenization treatment in the presence of HTAB and centrifugation treatment, and much time is also needed.

Further, in determining the white blood cell count of whole blood, in order to remove substances which hinder the measurement of myeloperoxidase, it is necessary to conduct an operation in which the white blood cells are separated from whole blood by using the Ficoll reagent or the like. Therefore, it is necessary to conduct the operation for removing substances which hinder the measurement and to perform a reaction for fixing the white blood cells, so that the procedure becomes cumbersome and it is necessary to use a number of reagents and special apparatuses.

Akiko GOTO, Ichio UCHIDA, Hitoshi TOMITA: "Rinsho Kensa (Clinical Examinations)", 40, 859–863 (1996) and Japanese Patent Application Laid-Open Specification Nos. 8-145993, 9-72906, 9-196919 and 11-32793 disclose a method for the counting of the white blood cells contained in the urine of a patient of a urinary tract infection. Specifically, in this method, a urine sample is treated with 0.05% Triton™ X-100, and the concentration of myeloperoxidase released from the white blood cells (95% of them are neutrophils) contained in the urine sample is measured by enzyme immunoassay.

The amount of cellular components in urine is extremely small, as compared to the amount of cellular components in blood. Therefore, in urine, the amount of substances which hinder the measurement of the concentration of myeloperoxidase is small. For this reason, in the above-mentioned method, a urine sample is treated only with Triton™ X-100 before the measurement of the concentration of myeloperoxidase released from the neutrophils contained in the urine sample. However, whole blood contains a mixture of white blood cells, red blood cells, platelets and plasma proteins and, hence, whole blood is a system containing various types of biological components in high concentrations. Therefore, it has been inconceivable that such method suitably applicable to a urine sample can be applied to whole blood.

There has been a report of the study in which whole blood is subjected to lysis treatment to thereby release peptides called "defensins" from the neutrophils in the whole blood, and the concentration of the released defensins is measured, and correlations between defensins and the white blood cell count and the neutrophil count are investigated (see Toshihiko Ihi, Masamitsu Nakazato, Hiroshi Mukae and Shigeru Matsukura: *Clinical Infection Diseases*, 25, 1134–1140 (1997)). However, in the method used in the abovementioned study, it is necessary to perform a cumbersome procedure that 1 M acetic acid is added to whole blood and the resultant mixture is homogenized by means of a polytron homogenizer, and the resultant is centrifuged under 2,000×g for 30 minutes at 4° C. thereby extracting the peptide. Therefore, this method cannot be practically used at all at sites of medical service where it is necessary to rapidly and easily determine the white blood cell count of a whole blood sample.

As described hereinabove, in the conventional methods for immunologically determining a substance derived from white blood cells, it is necessary to perform cumbersome and time-consuming operations, such as an operation in which the white blood cells are separated from whole blood, and an operation in which the white blood cells are subjected to lysis treatment under stringent conditions for a long time in order to substantially release a desired substance from the white blood cells. Further, the conventional methods have a problem in that the determined value is not necessarily well in agreement with a white blood cell count as directly measured by means of a blood cell counting apparatus.

International Patent Application Publication No. WO99/46599 (corresponding to Japanese Patent Application Laid- Open Specification No. 11-258231) (which was published after the filing date of the basic Japanese patent application of the present application) discloses a method in which a surfactant is added to a whole blood sample thereby releasing intrinsic elastase from the granulocytes, and the released elastase is measured by an immunological method using $\alpha_1$-antitrypsin inhibitor, which is an inhibitor against elastase, and the white blood cell count is determined, based on the concentration of the released elastase. However, in this method, for measuring the granulocyte elastase, it is necessary to perform an operation of adding $\alpha_1$-antitrypsin inhibitor. Therefore, this method is disadvantageous in that the procedure is cumbersome and the cost becomes high. Further, although a good correlation is present between the granulocyte elastase and the white blood cell count, the above-mentioned document has no description that this method is applied to a whole blood sample having a white blood cell count of 10,000 cells/$\mu$l or more, i.e., a whole blood sample obtained from a non-healthy human.

Thus, by any of the conventional methods, it is impossible that an intrinsic substance of the white blood cells is measured rapidly and easily by an immunological method and a white blood cell count of a whole blood sample is accurately determined without the need to separate the white blood cells from the whole blood sample. Also, by any of the conventional methods, it is impossible that, in addition to a white blood cell count of a whole blood sample, the concentration of CRP contained in the same whole blood sample is measured rapidly and easily.

SUMMARY OF THE INVENTION

The present inventors have made extensive and intensive studies with a view toward solving the above mentioned problems. As a result, it has surprisingly been found that the above object can be attained by a determination method in which a whole blood sample is mixed with a surfactant to thereby efficiently lyze the white blood cells and release intrinsic myeloperoxidase from the white blood cells, and the concentration of the released myeloperoxidase is measured. Specifically, it has unexpectedly been found that the myeloperoxidase concentration as measured by the above method exhibits a very good correlation with a white blood cell count as measured by the conventional aperture-impedance method, so that a white blood cell count can be determined, based on the myeloperoxidase concentration. Further, it has also been found that, in the above method, the concentration of C-reactive protein contained in the whole blood sample can also be measured in addition to the myeloperoxidase concentration. The present invention has been completed, based on these novel findings.

Therefore, it is a primary object of the present invention to provide a method for determining a white blood cell count of a whole blood sample rapidly and easily and at low cost.

The foregoing and other objects, features and advantages of the present invention will be apparent to those skilled in the art from the following detailed description and the appended claims taken in connection with the accompanying drawings.

DETAILED DESCRIPTION OF THE INVENTION

Figure 1:
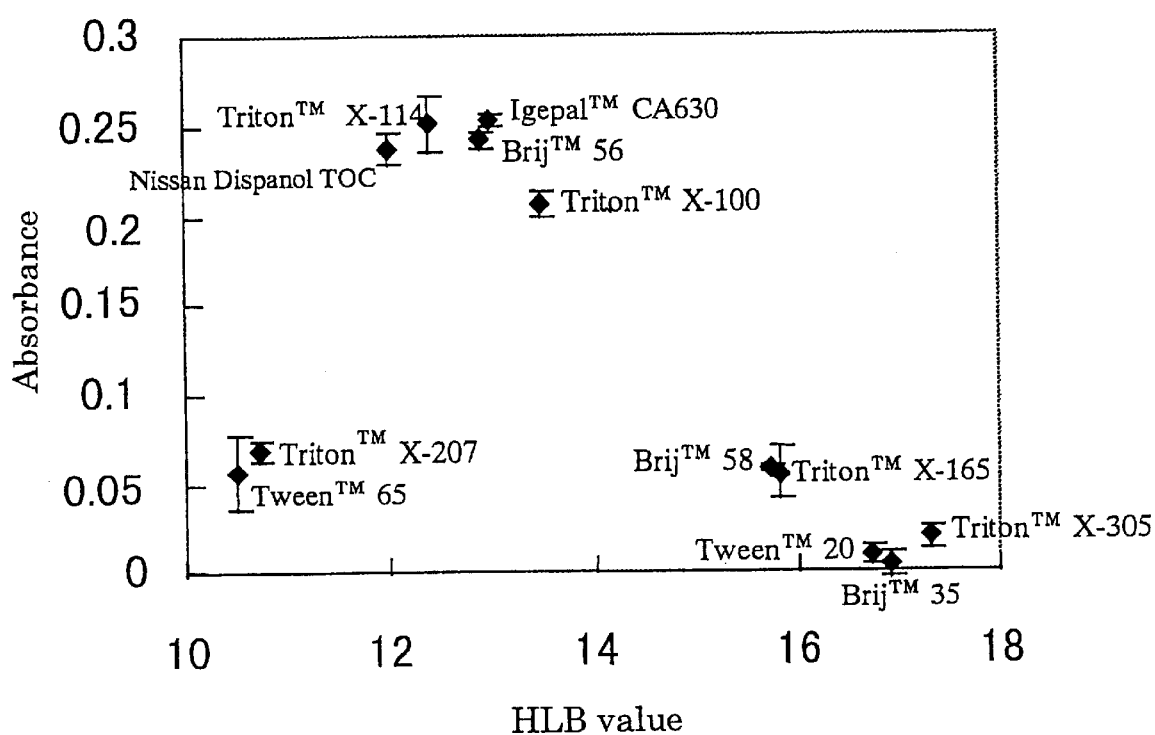
FIG. 1 is a diagram showing the relationship between the HLB value and the release amount (in terms of absorbance) of myeloperoxidase (MPO)

In the present invention, there is provided a method for determining a white blood cell count of a whole blood sample, which comprises:

(a) mixing a whole blood sample with a surfactant to thereby obtain a mixture;

(b) allowing the mixture to stand for a time sufficient to lyze the white blood cells contained in the whole blood sample and release intrinsic myeloperoxidase from the white blood cells;

(c) measuring the concentration of the released myeloperoxidase in the mixture; and (d) determining the white blood cell count in the whole blood sample, based on the concentration of the released myeloperoxidase.

For easy understanding of the present invention, the essential features and various preferred embodiments of the present invention are enumerated below.

1. A method for determining a white blood cell count of a whole blood sample, which comprises:
   (a) mixing a whole blood sample with a surfactant to thereby obtain a mixture;
   (b) allowing the mixture to stand for a time sufficient to lyze the white blood cells contained in the whole blood sample and release intrinsic myeloperoxidase from the white blood cells;
   (c) measuring the concentration of the released myeloperoxidase in the mixture; and
   (d) determining the white blood cell count in the whole blood-sample, based on the concentration of the released myeloperoxidase.

2. The method according to item 1 above, wherein, in step (c), the concentration of C-reactive protein contained in the whole blood sample is measured in addition to the concentration of the released myeloperoxidase.

3. The method according to item 1 above, wherein, in step (c), the concentration of the released myeloperoxidase is measured by an immunological method.

4. The method according to item 2 above, wherein, in step (c), both the concentration of the myeloperoxidase and the concentration of the C-reactive protein are measured by an immunological method.

5. The method according to item 3 or 4 above, wherein the immunological method is an enzyme immunoassay.

6. The method according to item 3 or 4 above, wherein the immunological method is an optical immunoassay.

7. The method according to any one of items 1 to 6 above, wherein the surfactant is a nonionic surfactant.

8. The method according to item 7 above, wherein the nonionic surfactant has a hydrophile-lipophile balance (HLB) value of from 12 to 14.

9. The method according to item 7 above, wherein the nonionic surfactant is a polyethylene oxide compound having a saturated or unsaturated hydrocarbon bonded thereto.

10. The method according to item 9 above, wherein the nonionic surfactant is at least one nonionic surfactant selected from the group consisting of a nonionic surfactant having a polyoxyethylene alkylphenyl ether structure, a nonionic surfactant which is a polyethylene oxide compound having an unsaturated aliphatic hydrocarbon bonded thereto, and a nonionic surfactant having a polyoxyethylene alkyl ether structure.

11. The method according to item 10 above, wherein the nonionic surfactant is at least one nonionic surfactant selected from the group consisting of Triton™ X-114, Triton™ X-100, Igepal™ CA630, Nissan Nonion NS-208.5, Nissan Dispanol TOC, Brij™ 97, and Brij™ 56.

12. The method according to any one of items 1 to 6 above, wherein the surfactant is at least one cationic surfactant selected from the group consisting of hexadecyltrimethylammonium bromide, hexadecyltrimethylammonium chloride, didecyldimethylammonium chloride, dodecyltrimethylammonium chloride, dodecyltrimethylammonium bromide, octadecyltrimethylammonium chloride, tetradecylammonium bromide, dodecylpyridinium chloride, hexadecylpyridinium chloride, hexadecylpyridinium bromide, 1-laurylpyridinium chloride, and tetradecyltrimethylammonium bromide.

13. The method according to any one of items 1 to 12 above, wherein the surfactant is mixed with the whole blood sample in an amount such that the concentration of the surfactant in the mixture is in the range of from 0.2 to 10% (w/v).

14. The method according to any one of items 1 to 13 above, wherein, in step (b), the mixture is allowed to stand for not more than 1 hour.

15. The method according to any one of items 1 to 14 above, wherein the white blood cell count is a neutrophil count.

Hereinbelow, the present invention is described in detail.

In the present invention, the term "whole blood" means blood containing all blood components, such as red blood cells, white blood cells, platelets and plasma. The term "white blood cell" is intended to cover neutrophils, monocytes, basophils, eosinophils and lymphocytes. The term "lysis of white blood cell" means to break the cell membranes of white blood cells, thereby releasing the contents of the cells to the outside of the cells.

For further illustrating the essential features of the present invention, the technical features included in the present invention will be described below in detail while explaining how the present invention has been developed.

As described in Borregaard, N. et al., "Granules of the human neutrophilic polymorphonuclear leukocytes": *Blood*, 89, 3503–3251 (1997), examples of substances present in neutrophils include substances present in azurophil granules (primary granules), specific granules (secondary granules), gelatinase granules (tertiary granules) and vesicles.

Specifically, examples of substances present in azurophil granules (primary granules) include CD63, CD68, V-type $H^+$ ATPase, acid $\beta$-glycerophosphatase, acid mucopolysaccharides, $\alpha_1$-antitrypsin, $\alpha_1$-mannosidase, azurocidin/CAP37/heparin-binding protein, bactericidal/permeability-increasing protein (BPI), $\beta$-glycerophosphatase, $\beta$-glucuronidase, cathepsin, defensins, neutrophil elastase, lysozyme, myeloperoxidase, N-acetyl-$\beta$-glucosaminidase, proteinase, sialidase and ubiquitin.

Examples of substances present in specific granules (secondary granules) include CD11b, CD15 antigen, CD66, CD67, cytochrome $b_{558}$, fMLP receptor, fibronectin receptor, G-protein $\alpha$-subunit, laminin receptor, NB-1 antigen, 19-kD protein, 155-kD protein, Rap 1, Rap 2, SCAMP, thrombospondin receptor, TNF receptor, urokinase type plasminogen activator receptor, VAMP-2, vitronectin receptor, $\beta_2$-microglobulin, collagenase, gelatinase, hCAP-18, histaminase, heparinase, lactoferrin, lysozyme, NGAL, urokinase type plasminogen activator receptor sialidase, SGP28 and vitamin $B_{12}$-binding protein.

Examples of substances present in gelatinase granules (tertiary granules) include CD11b, cytochrome $b_{558}$, diacylglycerol deacylase, fMLP receptor, SCAMP, urokinase type plasminogen activator receptor, VAMP-2, V-type $H^+$ ATPase, acetyltransferase, $\beta_2$-microglobulin, gelatinase and lysozyme.

Examples of substances present in vesicles include alkaline phosphatase, complement receptor, cytochrome $b_{558}$, CD11b, CD14, CD16, fMLP receptor, SCAMP, urokinase type plasminogen activator receptor, VAMP-2, V-type H+ ATPase, CD10, CD13, CD45, C1q receptor, DAF (decay accelerating factor) and plasma proteins (in-cluding tetranectin).

The present inventors considered that it is preferred that a substance which is measured for the purpose of the determination of a white blood cell count of whole blood has the properties that, when whole blood is treated with a surfactant, the substance is released in an amount sufficient for measurement thereof by enzyme immunoassay and that the amount of the substance in whole blood does not exhibit a great fluctuation even in the presence of a primary disease other than an infection. From such viewpoint, the present inventors made studies, and, as a result, they considered that the substance which is measured for the purpose of the determination of a white blood cell count of whole blood is desired to be selected from the substances present in azurophil granules (primary granules) or specific granules (secondary granules), and is especially desired to be selected from myeloperoxidase (hereinafter, frequently referred to as "MPO"), neutrophil elastase (hereinafter, frequently referred to as "ELT") and lactoferrin (hereinafter, frequently referred to as "LTF").

Further, the present inventors conducted the following studies. Whole blood samples each having a white blood cell count of less than 10,000 cells/µl were obtained from a group of healthy humans, and whole blood samples each having a white blood cell count of 10,000 cells/µl or more were obtained from a group of non-healthy humans. These whole blood samples were individually examined, and the correlation between each of the concentrations of MPO, ELT and LTF and the white blood cell count was analyzed. It was found that with respect to the whole blood samples obtained from the group of healthy humans, the correlation coefficient (R) of the relationship between the MPO concentration and the white blood cell count was extremely high, specifically R=0.9336, as compared to the correlation coefficient (R) of the relationship between the concentration of LTF or ELT and the white blood cell count. Therefore, it was found that, in the case of whole blood samples obtained from healthy humans, most accurate determination of a white blood cell count can be obtained by measuring the MPO concentration.

Further, with respect to the data of the whole blood samples obtained from the group of non-healthy humans, attention was paid to the gradient of a regression line showing the correlation between each of the MPO, LTF and ELT concentrations and the white blood cell count. The gradients of the regression lines of the MPO, LTF and ELT concentrations versus the white blood cell count in the whole blood samples obtained from non-healthy humans were, respectively, compared to the gradients of the regression lines of the MPO, LTF and ELT concentrations versus the white blood cell count in the whole blood samples obtained from healthy humans. The comparison showed the following. The gradient of the regression line showing the correlation between the MPO concentration and the white blood cell count in the non-healthy human whole blood was 0.0019, which is close to the gradient (0.0021) of the regression line showing the correlation between the MPO concentration and the white blood cell count in the healthy human whole blood. To the contrary, the gradient of the regression line showing the correlation between the LTF concentration and the white blood cell count in the non-healthy human whole blood was 0.0007, in contrast to 0.0016 which is the gradient of the regression line showing the correlation between the LTF concentration and the white blood cell count in the healthy human whole blood, that is, it was shown that, in the case of LTF, the gradient of the regression line obtained with respect to the non-healthy human whole blood was as small as about 1/2.3 of the gradient of the regression line obtained with respect to the healthy human whole blood. Further, the gradient of the regression line showing the correlation between the ELT concentration and the white blood cell count in the non-healthy human whole blood was 0.0031, in contrast to 0.0017 which is the gradient of the regression line showing the correlation between the ELT concentration and the white blood cell count in the healthy human whole blood, that is, it was shown that, in the case of ELT, the gradient of the regression line obtained with respect to the non-healthy human whole blood was as large as about 1.8 times the gradient of the regression line obtained with respect to the healthy human whole blood. In addition, it was also found that, in the case of a whole blood sample obtained from a patient suffering from acute pancreatitis, the ELT concentration was extremely higher than the concentrations of MPO and LTF, and the ELT concentration exhibited a great deviation from a regression line showing the correlation between the ELT concentration and the white blood cell count in whole blood. Thus, there were obtained results indicating a tendency wherein, in the case of diseases which result in raising the white blood cell count of whole blood to as high as 10,000 cells/µl or more, the amount of intrinsic MPO does not exhibit a significant change, but the amount of intrinsic LTF decreases and the amount of intrinsic ELT increases. However, the reason for such tendency has not yet been elucidated.

For obtaining an accurate determination of a white blood cell count of whole blood, it is important to use a determination method which produces results such that the gradient of a regression line obtained with respect to whole blood exhibits no variation depending on whether the whole blood is healthy human whole blood having a white blood cell count of less than 10,000 cells/µl or the whole blood is non-healthy human whole blood having a white blood cell count of 10,000 cells/µl or more. Therefore, in view of the above-described results of the studies conducted by the present inventors, it was concluded that, for accurately determining a white blood cell count of a whole blood sample, it is most appropriate to measure the amount of myeloperoxidase contained in the whole blood sample.

As a result of the intensive and extensive studies as described above, the present inventors found that the amount of myeloperoxidase is useful as an index of a white blood cell count. Based on these studies, the present invention has been completed.

The present invention provides a method for determining a white blood cell count of a whole blood sample, in which a whole blood sample is mixed with a surfactant to thereby lyze the white blood cells and release intrinsic myeloperoxidase from the white blood cells, and the concentration of the released myeloperoxidase is measured. Specifically, the present invention provides a method for determining a white blood cell count of a whole blood sample, which comprises:

(a) mixing a whole blood sample with a surfactant to thereby obtain a mixture;

(b)) allowing the mixture to stand for a time sufficient to lyze the white blood cells contained in the whole blood sample and release intrinsic myeloperoxidase from the white blood cells;

(c) measuring the concentration of the released myeloperoxidase in the mixture; and (d) determining the white blood cell count in the whole blood sample, based on the concentration of the released myeloperoxidase.

In the method of the present invention, a whole blood sample is mixed with a surfactant to thereby obtain a mixture, and the obtained mixture is allowed to stand to thereby lyze the white blood cells, the red blood cells, the platelets and the like contained in the whole blood sample.

In the present invention, the term "surfactant" means a compound which has both a hydrophilic moiety and a lipophilic moiety in a single molecule. Herein, "surfactant" means a water-soluble surfactant, unless otherwise indicated.

In general, surfactants are roughly classified into ionic surfactants and nonionic surfactants. In the method of the present invention, as a surfactant which is mixed with a whole blood sample to thereby lyze the white blood cells, any of an ionic surfactant and a nonionic surfactant can be used.

Ionic surfactants can be classified into anionic surfactants, cationic surfactants and amphoteric surfactants.

Examples of anionic surfactants include sodium dodecyl sulfate, sodium dodecyl sulfonate, sodium dodecyl-N-sarcosinate, sodium cholate, sodium deoxycholate, and sodium taurodeoxycholate.

Examples of cationic surfactants include hexadecyltrimethylammonium bromide, hexadecyltrimethylammonium chloride, didecyldimethylammonium chloride, didecyldimethylammonium bromide, dodecyltrimethylammonium chloride, dodecyltrimethylammonium bromide, octadecyltrimethylammonium chloride, octadecyltrimethylammonium bromide, tetradecylammonium bromide, dodecylpyridinium chloride, hexadecylpyridinium chloride, hexadecylpyridinium bromide, 1-laurylpyridinium chloride, and tetradecyltrimethylammonium bromide.

Examples of amphoteric surfactants include 3-[(3-cholamidopropyl)dimethylammonio]-1-propanesulfonic acid, 3-[(3-cholamidopropyl)dimethylammonio]-2-hydroxy-1-propanesulfonic acid, palmitoyl lysolecithin, dodecyl-N-betaine, and dodecyl-β-alanine.

Examples of nonionic surfactants include octyl glucoside, heptyl thioglucoside, decanoyl-N-methylglucamide, polyoxyethylene dodecyl ether, polyoxyethylene heptamethyl hexyl ether, polyoxyethylene isooctyl phenyl ether, polyoxyethylene nonyl phenyl ether, a fatty acid ester of polyoxyethylene, a fatty acid ester of sucrose, and polyoxyethylene sorbitol ester.

With respect to the surfactant used in the method of the present invention, it is desired that the surfactant can serve to release intrinsic MPO from white blood cells while holding down denaturation of the MPO to a level as low as possible. From this viewpoint, it is preferred that the surfactant is a nonionic surfactant, rather than an ionic surfactant, which has a high surface active property.

As one of the parameters showing the properties of a surfactant, there can be mentioned the hydrophilelipophile balance (HLB). An HLB value is an index of the balance between the hydrophilic group and the lipophilic group in the surfactant molecule. The concept of the HLB value was proposed by Griffin. The HLB value of a surfactant is experimentally determined by evaluating the emulsifying ability of the surfactant and conducting a simple calculation (see, for example, "Sin-ban Kaimen-Kassei-Zai Handobukku (New Edition, Surfactant Handbook)", edited by Tokiyuki YOSHIDA, Shin-ichi SHINDO, Tadayoshi OOGAKI and Mikiyoshi YAMANAKA and published by Kogaku Tosho Co., Japan (1987)). The HLB values of examples of surfactants which can be used in the method of the present invention are shown below.

| Surfactant | HLB value |
| --- | --- |
| Nissan Nonion NS-204.5 | 9.5 |
| Triton X-45 | 10.4 |
| Triton X-207 | 10.7 |
| Nissan Nonion NS-206 | 10.9 |
| Nissan Nonion HS-206 | 11.2 |
| Nissan Dispanol TOC | 12.0 |
| Triton X-114 | 12.4 |
| Brij 97 | 12.4 |
| Nissan Nonion NS-208.5 | 12.6 |
| Brij 56 | 12.9 |
| Igepal CA630 | 13.0 |
| Nonidet P-40 | 13.0 |
| Nissan Nonion HS-210 | 13.3 |
| Triton X-100 | 13.5 |
| Nissan Nonion NS-212 | 14.1 |
| Igepal CA720 | 14.6 |
| Nissan Nonion HS-215 | 15.0 |
| Nissan Nonion NS-215 | 15.0 |

It is preferred that the nonionic surfactant used in the method of the present invention has an HLB value of from 12 to 14. Nonionic surfactants having an HLB value of from 12 to 14 can exhibit a high efficiency for releasing intrinsic MPO from the white blood cells contained in the whole blood sample. When the nonionic surfactant has an HLB value which is higher than 14, the nonionic surfactant exhibits a markedly low efficiency for releasing intrinsic MPO from the white blood cells contained in the whole blood sample. On the other hand, when the nonionic surfactant has an HLB value which is lower than 12, the nonionic surfactant exhibits poor solubility in water, so that not only does the efficiency for releasing intrinsic MPO from the white blood cells become low, but also the handling of the surfactant becomes difficult. The HLB values mentioned herein are those described in "HANDBOOK OF INDUSTRIAL SURFACTANTS" Second Edition, edited by Michael and Irene Ash and published by Gower Publishing Limited (1997), unless otherwise indicated.

From the viewpoint of efficiently releasing intrinsic MPO from the white blood cells, it is preferred that the nonionic surfactant is a polyethylene oxide compound having a saturated or unsaturated hydrocarbon bonded thereto. It is more preferred that the nonionic surfactant is selected from the group consisting of:

a nonionic surfactant having a polyoxyethylene alkylphenyl ether structure (for example, Triton™ X-114 (manufactured and sold by Nacalai Tesque, Inc., Japan), Triton™ X-100 (manufactured and sold under the brand of SIGMA™, U.S.A.), Igepal™ CA630 (manufactured and sold under the brand of SIGMA™, U.S.A.), and Nissan Nonion NS-208.5 (manufactured and sold by Nippon Oil and Fats Co., Ltd., Japan)), a nonionic surfactant which is a polyethylene oxide compound having an unsaturated aliphatic hydrocarbon bonded thereto (for example, Brij™ 97 (manufactured and sold under the brand of SIGMA™, U.S.A.)), and a nonionic surfactant having a polyoxyethylene alkyl ether structure (for example, Nissan Dispanol TOC (manufactured and sold by Nippon Oil and Fats Co., Ltd., Japan), and Brij™ 56 (manufactured and sold under the brand of SIGMA™, U.S.A.)). It is more preferred that the nonionic surfactant is Triton™ X-114, since it exhibits the high activity to release intrinsic MPO from the white blood cells and enables highly sensitive measurement of intrinsic MPO.

For reference, with respect to the surfactants shown above with the trade names, their CTFA (The Cosmetic, Toiletry and Fragrance Assoc.) identifications and/or IUPAC identifications are summarized in the table below.

| Trade name | CTFA identification | IUPAC identification |
|---|---|---|
| Triton ™ X-114 | Octoxynol-8 | α-[4-(1,1,3,3,-Tetramethylbutyl)phenyl]-ω-hydroxypoly(oxy-1,2-ethanediyl) |
| Triton ™ X-100 | Octoxynol-9 | α-[4-(1,1,3,3,-Tetramethylbutyl)phenyl]-ω-hydroxypoly(oxy-1,2-ethanediyl) |
| Igepal ™ CA630 | Octoxynol-9 | α-[4-(1,1,3,3,-Tetramethylbutyl)phenyl]-ω-hydroxypoly(oxy-1,2-ethanediyl) |
| Nissan Nonion NS-208.5 | Nonoxynol-8.5 | α-(4-Nonylphenyl)-ω-hydroxypoly(oxy-1,2-ethanediyl) |
| Nissan Dispanol TOC | Polyoxyethylene alkyl ether | — |
| Brij ™ 97 | Polyoxyethylene oleilalchol (Oleth-10) | — |
| Brij ™ 56 | Polyoxyethylene cetylalchol (Ceteth-10) | — |

In the method of the present invention, the surfactant employed to lyze the white blood cells and release intrinsic MPO from the white blood cells may be a cationic surfactant. From the results of the experiments conducted by the present inventors, the present inventors have found that, for releasing intrinsic MPO from the white blood cells, it is suitable to use a cationic surfactant selected from the group consisting of hexadecyltrimethylammonium bromide, hexadecyltrimethylammonium chloride, didecyldimethylammonium chloride, dodecyltrimethylammonium chloride, dodecyltrimethylammonium bromide, octadecyltrimethylammonium chloride, tetradecylammonium bromide, dodecylpyridinium chloride, hexadecylpyridinium chloride, hexadecylpyridinium bromide, 1-laurylpyridinium chloride, and tetradecyltrimethylammonium bromide.

In the method of the present invention, it is preferred that the surfactant is mixed with the whole blood sample in an amount such that the concentration of the surfactant in the resultant mixture is 0.2% (w/v) or more. When the concentration of the surfactant in the mixture is less than 0.2% (w/v), it is impossible to obtain a satisfactory release of intrinsic MPO from the white blood cells. On the other hand, when the concentration of the surfactant in the mixture is too high, not only does the cost for the surfactant become high because of the use thereof in an increased amount, but also the handling of the mixture becomes difficult. Therefore, it is preferred that the surfactant is mixed with the whole blood sample in an amount such that the concentration of the surfactant in the resultant mixture is in the range of from 0.2 to 10% (w/v), more advantageously from 0.2 to 5.0% (w/v), still more advantageously from 0.2 to 2.0% (w/v).

In the method of the present invention, with respect to the method for mixing a whole blood sample with a surfactant, there is no particular limitation, as long as the mixing method surely enables the operation in which a whole blood sample is mixed with a surfactant to thereby obtain a mixture, and the mixture is allowed to stand to thereby lyze the white blood cells contained in the whole blood sample and release intrinsic myeloperoxidase from the white blood cells. For example, the mixing can be performed by a method in which an aqueous solution of a surfactant is prepared, and the aqueous solution of a surfactant is added to a whole blood sample. In this case, after the addition of the aqueous solution of a surfactant, the resultant mixture may be either stirred or not stirred. Alternatively, the mixing can also be performed by a method in which a surfactant in particulate form is attached to the inside surface of a mixing vessel, and a whole blood sample is added to the mixing vessel. Also in the case of this mixing method, by the mixing between the whole blood sample and the surfactant, the white blood cells are lyzed and intrinsic myeloperoxidase is released from the white blood cells. Also in this mixing method, the mixture of the whole blood sample and the surfactant may be either stirred or not stirred.

In the step in which the mixture obtained by mixing a whole blood sample with a surfactant is allowed to stand, there is no particular limitation with respect to the standing time of the mixture as long as the time is sufficient to lyze the white blood cells contained in the whole blood sample and release intrinsic myeloperoxidase from the white blood cells. However, in the method of the present invention, it is preferred that the standing time of the mixture is not larger than 1 hour. Generally, the standing time is in the range of from about 1 minute to 1 hour. In the initial steps of diagnosis of a patient suffering from an infectious disease, since it is necessary that an appropriate treatment, such as the administration of a pharmaceutical, be performed as soon as possible, it is necessary to rapidly obtain the determination of a white blood cell count (and the concentration of CRP). Therefore, for shortening the time required for the determination of a white blood cell count, it is preferred that the standing time of the mixture is short.

In the method of the present invention, with respect to the temperature at which the mixture obtained by mixing a whole blood sample with a surfactant is allowed to stand, there is no particular limitation. However, since the lysis of the white blood cells and the release of intrinsic myeloperoxidase from the white blood cells are performed in an aqueous dispersion (emulsion), it is not desired to cool the above-mentioned mixture to a temperature at which the mixture is frozen. Also, it is not desired to heat the above-mentioned mixture to a high temperature at which the antigenicity of MPO is altered, since an alteration in the antigenicity of MPO hinders the immunological reaction of MPO. Therefore, in the method of the present invention, it is preferred that the temperature at which the mixture obtained by mixing a whole blood sample with a surfactant is allowed to stand is in the range of from 0° C. to room temperature (about 25° C.). Further, in view of the fact that the diagnosis of an infectious disease is conducted in an ordinary clinic, it is more preferred that the temperature at which the above-mentioned mixture is allowed to stand is room temperature.

In the method of the present invention, the mixture obtained by mixing a whole blood sample with a surfactant can be subjected to the measurement of the concentration of C-reactive protein contained in the whole blood sample in addition to the measurement of the concentration of the released myeloperoxidase. With respect to the CRP value of the healthy human (standard range), reports have been made by various researchers; examples of reported values of the standard range are as follows: 60.3 μg/dl or less (Yasuko YAMAGISHI et al: "Rinsho Byori (Clinical Pathology)" 32: 1389–1394, 1984); 300 μg/dl or less (Akira NISHIDA: "Kitasato Igaku (Kitasato Medicine)" 16: 393–401, 1986); and 4.0 to 235.3 μg/dl (Naoto SHIMETANI: "Kitasato Igaku (Kitasato Medicine)" 24: 97–103, 1994). The CRP value of the healthy human (standard range) is also described in handbooks concerning the data obtained by clinical examinations. For example, in the handbook entitled "Rinsho-ni- Yakudatsu Kensa-chi-no Yomikata•Kangaekata (How to read and consider clinical examination data in a clinically useful manner)", compiled under the supervision of Kin-ya KAWANO and Osamu NISHIZAKI and published by Sogo-Igakusha Co., Japan, p.236, 1997), it is described that the CRP value of the healthy human (standard range) is 0.3 mg/dl (=3 µg/ml) or less (although the value varies to some extent depending on the determination method). When monocytes/macrophages are activated by a lesion, such as inflammation and cancer, monocytes/macrophages secrete interleukin 6, interleukin 1, TNF-α and the like, and, as a result, the production of acute phase proteins, such CRP, is induced in hepatocytes, so that the CRP concentration of the blood is elevated. The elevation of the CRP concentration of the blood is a non-specific reaction. However, the CRP concentration of the blood sensitively responds to a lesion and hence is a most widely used type of inflammation marker. Further, the CRP concentration of the blood elevates in accordance with the progression of cancer and hence is also useful as a tumor marker in the broad sense. Also, with respect to infectious diseases, the blood in the case of a bacterial infection exhibits a CRP concentration which is higher than in the case of a viral infection. Therefore, by measuring the CRP concentration in addition to the determination of a white blood cell count, more precise diagnosis can be made. For example, the below-indicated relationships are known between the CRP value and pathological conditions.

| CRP (µg/ml) | Pathological conditions |
| --- | --- |
| 0 to 20 | pregnancy, smoking, acute appendicitis, etc. |
| 0 to 100 | malignant tumor, viral infection, systemic lupus erythematosus, etc. |
| 20 to 200 | bacterial infection, chronic rheumatoid arthritis, etc. |
| 20 to 200 or more | sepsis, pneumonia, and angitis |

In the method of the present invention, with respect to the method for measuring the concentration of the MPO released from the white blood cells, there is no particular limitation. The MPO concentration can be measured by various methods. Specific examples of methods for measuring the MPO concentration include the measurement of the enzyme activity of MPO, liquid chromatography and an immunological method. However, it is preferred that the MPO concentration is measured by an immunological method, since an immunological method is high in the sensitivity and specificity of the measurement and can also be used to measure the CRP concentration.

In the present invention, the term "immunological method" is intended to cover, for example, the following methods: a method in which the amount of an antigen or antibody is measured using, as a marker, enzyme activity or radioactivity; a method in which the amount of an antigen or antibody is measured by detecting an immune complex formed by an antigen-antibody reaction; and a method in which an antigen or antibody is carried on a carrier, such as latex beads or colloidal gold, and the carrier-supported antigen or antibody is subjected to agglutination with an antibody or antigen, and the results of the agglutination are examined to measure the extent of the antigen-antibody reaction, and the amount of an antigen or antibody is measured, based on the extent of the antigen-antibody reaction.

With respect to the type of the immunological method used in the method of the present invention, there is no particular limitation. However, from the viewpoint of safety, it is not desired to use an immunological method using radioactivity as a marker.

As specific examples of immunological methods, there can be mentioned immunochromatography (which is used in the art to measure the amount of proteins and the like); an enzyme immunoassay using a 96-well plate; and the measuring method (the optical immunoassay of BioStar, U.S.A.) described in International Application Publication Nos. WO91/04491, WO92/14136, WO92/14147, WO92/16826 and WO94/03774.

A specific explanation is made below with respect to the method for measuring the MPO concentration by immunochromatography. An anti-human MPO antibody is immobilized on a substrate membrane by adsorption or by a chemical method, wherein the substrate membrane is comprised of cellulose, nitrocellulose or a cellulose having its surface chemically modified (a cellulose which has been chemically modified to have a cationic functional group, such as an amino group or a diethylaminoethyl group or to have an anionic functional group, such as a carboxyl group). The substrate having the antibody immobilized thereon is immersed in a buffer solution containing bovine serum albumin or the like to thereby effect a blocking reaction, and then dried to obtain a chip for use in immunochromatography for measuring MPO.

In the above-described production of the chip for use in immunochromatography, when an anti-human CRP antibody is immobilized on the substrate in addition to the anti-human MPO antibody (wherein the 2 antibodies may be immobilized at different positions on a single substrate or may be immobilized respectively on 2 substrates disposed side by side), there can be obtained a chip for use in immunochromatography for measuring MPO and CRP.

The detection of MPO (and CRP) can be effected using an anti-human MPO antibody (and anti-human CRP antibody) which has been labeled with colloidal gold or latex beads. Specifically, the detection can be made as follows. The above-mentioned labeled antibody is mixed with the (whole blood sample/surfactant) mixture containing the lyzed white blood cells, and the resultant mixture is dropped on the substrate in the abovementioned chip for use in immunochromatography, and, then, an appropriate developing buffer is added thereto, so that the dropped mixture moves and develops on the surface of the substrate in the chip. The (whole blood sample/surfactant) mixture containing the lyzed white blood cells may be previously diluted to an appropriate extent. During the moving/developing of the dropped mixture, an immune complex of the labeled antibody and MPO (and CRP) is captured by the immobilized antibody and exhibits coloring. The concentration of MPO (and CRP) can be measured by evaluating the degree of the coloring or by using an optical measurement apparatus.

Next, an explanation is made below with respect to the method for measuring the MPO concentration and CRP concentration by an enzyme immunoassay using a 96-well plate. First, an anti-human MPO antibody and an anti-human CRP antibody as primary antibodies are immobilized on a commercially available 96-well plate as a substrate. On the other hand, the (whole blood sample/surfactant) mixture containing the lyzed white blood cells is diluted 2,000-fold to 4,000-fold, and the resultant diluted mixture is added to the above-mentioned 96-well plate to thereby effect an antigen-antibody reaction between the immobilized antibodies on the plate and the MPO and CRP in the diluted mixture.

Subsequently, a solution of an anti-human MPO antibody and a solution of an anti-human CRP antibody (as secondary antibodies) which antibodies have been labeled with an enzyme, such as horseradish peroxidase (HRP) or alkaline phosphatase, are added to the plate to thereby effect an antigen-antibody reaction using the secondary antibodies. Then, either a solution containing tetramethylbenzidine (TMB) and $H_2O_2$, which are substrates for HRP, or a solution containing p-nitrophenyl phosphate, which is a substrate for alkaline phosphatase, is added thereto to effect coloring. After a predetermined period of time, 1 N sulfuric acid or a sodium hydroxide solution is added thereto to terminate the reaction. By measuring the absorbance of the colored reaction mixture, the MPO concentration and the CRP concentration can be measured.

The method for measuring the MPO concentration and CRP concentration by an optical immunoassay can be performed in accordance with the description of Covalciuc K A, Webb K H and Carlson C A: *Journal of Clinical Microbiology* 12:3971–3974 (1999). Specifically, this method is conducted as follows. A silicon wafer is provided. A thin film of a substance having a refractive index which is different from the refractive index of the silicon wafer (e.g., a thin film of a polymer, such as polysiloxane, or of diamond-like carbon) is formed on the surface of the wafer. Then, an anti-human MPO antibody and an anti-human CRP antibody as primary antibodies are immobilized on the surface of the above silicon wafer having the thin film thereon. The (whole blood sample/surfactant) mixture containing the lyzed white blood cells is diluted 100-fold to 200-fold, and the resultant diluted mixture is mixed with a solution of an HRP-labeled anti-human MPO antibody and a solution of an HRP-labeled anti-human CRP antibody, and the resultant mixture is added to the surface of the silicon wafer to thereby effect an antigen-antibody reaction between the immobilized antibodies on the silicon wafer and the MPO and CRP in the diluted mixture. Subsequently, "TMB fast" (manufactured and sold by Kirkegaad & Perry Laboratories Inc., U.S.A.) (which is a TMB precipitation substrate) is added thereto, and the resultant is allowed to stand for a predetermined period of time, thereby forming a precipitation layer on the surface of the silicon wafer. From the variation in the interference colors due to the thickness of the precipitation layer formed on the surface of the silicon wafer, the MPO concentration and CRP concentration can be determined. Alternatively, the MPO concentration and CRP concentration can also be determined by measuring the thickness of the precipitation layer formed on the surface of the silicon wafer, by means of an ellipsometer.

In the method of the present invention, the white blood cell count in the whole blood sample is determined, based on the thus measured concentration of MPO. With respect to the method for determining the white blood cell count, based on the MPO concentration, there is no particular limitation. The methods which are generally used in the art can be employed. Specifically, as conducted in Example 10 of the present specification, the white blood cell count can be determined from a regression line showing the correlation between the MPO concentration and the white blood cell count.

Further, in the method of the present invention, it is preferred that the white blood cell count determined by the method of the present invention is a neutrophil count. Neutrophils are the cells which are present in a largest ratio among all types of white blood cells. It is known that, when a bacterial infection or an inflammation occurs, the number of neutrophils in the blood is increased. Therefore, when it is intended to judge the presence or absence of a bacterial infectious disease or judge the graveness of an inflammation, it is preferred to determine a neutrophil count. As described in Examples 7, 9 and 10 of the present specification, when a whole blood sample is mixed with a surfactant to thereby lyze the white blood cells and release intrinsic MPO from the white blood cells, the concentration of the released MPO exhibits a high correlation not only with a white blood cell count but also with a neutrophil count. Therefore, by the method of the present invention, a neutrophil count can be determined as well as a white blood cell count.

BEST MODE FOR CARRYING OUT THE INVENTION

Hereinbelow, the present invention will be described in more detail with reference to the following Examples and Comparative Examples, but they should not be construed as limiting the scope of the present invention.

EXAMPLE 1

Experiments to Determine the Time Required for Lyzing White Blood Cells 10 ml of healthy human whole blood was collected in a test tube containing 10 mg of EDTA-2K (manufactured and sold by Dojin Laboratories, Japan) and the resultant EDTA-containing whole blood sample was stirred well, and then 1 ml of the whole blood sample was taken out from the test tube. To the 1 ml whole blood sample taken out from the test tube was added 100 $\mu$l of an aqueous 11% solution of Triton™ X-100 (manufactured and sold under the brand of SIGMA™, U.S.A.), and the resultant mixture was stirred well and then allowed to stand at room temperature for 1 minute to obtain a (whole blood sample/surfactant) mixture containing the lyzed white blood cells. Substantially the same operation as mentioned above was repeated except that the standing time at room temperature was changed to 5 minutes, 30 minutes and 60 minutes to thereby lyze the white blood cells contained in the whole blood.

After the above-mentioned period of time, each of the obtained (whole blood sample/surfactant) mixtures containing the lyzed white blood cells was individually diluted 2,000-fold with a sample diluting buffer (20 mM phosphate buffer (pH 7.4) containing 0.1% bovine serum albumin and 0.2% sodium azide), which buffer is attached to BIOXYTEC™ MPO Enzyme Immunoassay kit (manufactured and sold by OXIS International, Inc., U.S.A.), and the resultant diluted mixture was taken as a sample for the measurement of myeloperoxidase (MPO).

With respect to the above-mentioned sample for the measurement of MPO and a standard MPO solution (which is obtained by dissolving commercially available MPO in the above mentioned buffer), the measurement of the MPO concentration was performed using BIOXYTEC™ MPO Enzyme Immunoassay kit (manufactured and sold by OXIS International, Inc., U.S.A.) in accordance with the instruction manual attached thereto.

Specifically, with respect to the measurement of the MPO concentration of the above-mentioned sample, MPO (manufactured and sold by Elastin Products Co., INC., U.S.A.) was added to the sample so that the final concentration of the added MPO became 5 ng/ml or 10 ng/ml, and the resultant mixture was measured with respect to the MPO concentration. From the obtained value of MPO concentration, a calibration curve for each sample was obtained. The obtained calibration curve was corrected, based on its relationship with a calibration curve obtained with respect to the standard MPO solution, and the corrected calibration curve of each sample was used to determine the MPO concentration of the whole blood. The measurement was conducted 3 times, and a mean value±standard deviation was obtained. The results are shown in Table 1.

TABLE 1

| Treatment time with Triton ™ X-100 | MPO concentration of whole blood ($\mu$g/ml) |
|---|---|
| 1 minute | 9.88 ± 0.50 |
| 5 minutes | 10.17 ± 0.63 |
| 30 minutes | 9.94 ± 0.72 |
| 60 minutes | 10.01 ± 0.22 |

Thus, it was confirmed that, in the case of the treatment with Triton™ X-100, MPO can be released from the white blood cells to a satisfactory extent within 60 minutes from the start of the treatment.

EXAMPLE 2

The Concentration of a Surfactant and the Release Amount of MPO 10 ml of healthy human whole blood was collected and immediately mixed with 10 mg of EDTA-2K (manufactured and sold by Dojin Laboratories, Japan), and the resultant EDTA-containing whole blood sample was subjected to the below-described various measurements within 1 hour from the blood collection.

The myeloperoxidase concentration was measured by the following method.

500 $\mu$l of the blood was put in a 2-ml Eppendorf tube, and 500 $\mu$l of an aqueous surfactant solution having a surfactant concentration of 0.1, 0.2, 0.4, 0.6, 1, 2, 4, 10 or 20% (w/v) was added to the tube, and the resultant mixture was stirred for 2 seconds by a Vortex mixer. Subsequently, the mixture was allowed to stand for 60 minutes on ice to thereby lyze the white blood cells. As the above-mentioned surfactant, the below-mentioned 3 types of surfactants were individually used: Triton™ X-114 (manufactured and sold by Nacalai Tesque, Inc., Japan), Triton™ X-100 (manufactured and sold under the brand of SIGMA™, U.S.A.), and Igepal™ CA630 (manufactured and sold under the brand of SIGMA™, U.S.A.). After the lysis of the white blood cells, 100 $\mu$l of the mixture was taken out and added to 900 $\mu$l of a PBS solution containing dissolved therein 1% BSA (trade name: "Sigma fraction V", manufactured and sold under the brand of SIGMA™, U.S.A.). The resultant mixture was stirred by a Vortex mixer, and then 10 $\mu$l of the mixture was taken out and diluted 2,000-fold with 1% BSA/PBS solution. The resultant diluted mixture was subjected to a measurement by ELISA.

The outline of the ELISA is as follows. A 5 $\mu$g/ml PBS solution of a rabbit anti-human myeloperoxidase antibody (manufactured and sold by Calbiochem-Novabiochem Corporation, U.S.A.)(hereinafter, frequently referred to as "anti-MPO antibody") was put into the wells of a Nunc Immuno Plate (manufactured and sold by Nalge Nunc International, Denmark) in an amount of 100 $\mu$l per well. The solution in each well was sealed and subjected to a reaction for 18 hours at 4° C. thereby immobilizing the primary antibody. The wells were washed with a washing solution (0.05% Tween™ 20/PBS) and then subjected to blocking for 1 hour at room temperature by using 200 $\mu$l of a blocking solution (1% BSA/PBS), and then washed twice with the washing solution. Then, the above-obtained diluted mixture (blood sample which had been treated with a surfactant and then diluted) was put in the wells in an amount of 100 $\mu$l per well, and subjected to a reaction for 2 hours at room temperature. Then, the wells were washed 3 times with the washing solution, and a 5 $\mu$g/ml solution of an anti-MPO antibody labeled with horseradish peroxidase (hereinafter referred to as "HRP") was put in the wells in an amount of 100 $\mu$l per well, and subjected to a reaction for 1 hour at room temperature. As the above-mentioned HRP-labeled anti-MPO antibody, an anti-human MPO antibody (manufactured and sold by Calbiochem-Novabiochem Corporation, U.S.A.) which had been labeled with HRP Grade IV (manufactured and sold under the brand of SIGMA™, U.S.A.) was employed. The labeling was performed by the method described in Analytical Biochemistry, 132, 68–73 (1983). The wells were washed 5 times with the washing solution, and 100 1 $\mu$l of a just-prepared TMB solution (manufactured and sold by Kirkegaad & Perry Laboratories, U.S.A.) was added thereto to effect a color reaction. 2 Minutes after the start of the color reaction, 100 $\mu$l of a 1 N sulfuric acid solution (manufactured and sold by Nacalai Tesque, Inc., Japan) was added to the wells to thereby terminate the reaction. Then, the absorbance at 450 nm was measured by means of a plate reader (manufactured and sold by Bio-Rad Laboratories, U.S.A.). The measurement was conducted 3 times, and a mean value±standard deviation was obtained. The results are shown in Table 2.

TABLE 2

| Concentration of surfactant | Release amount of MPO in whole blood (Abs. 450 nm) | | |
|---|---|---|---|
| (% (w/v)) | Triton ™ X-100 | Triton ™ X-114 | Igepal ™ CA630 |
| 0.00 | 0.082 ± 0.002 | 0.101 ± 0.014 | 0.082 ± 0.006 |
| 0.05 | 0.104 ± 0.005 | 0.120 ± 0.026 | 0.103 ± 0.005 |
| 0.10 | 0.161 ± 0.009 | 0.131 ± 0.016 | 0.156 ± 0.009 |
| 0.20 | 0.202 ± 0.006 | 0.207 ± 0.004 | 0.205 ± 0.007 |
| 0.30 | 0.228 ± 0.009 | 0.198 ± 0.003 | 0.211 ± 0.008 |
| 0.50 | 0.262 ± 0.005 | 0.259 ± 0.007 | 0.249 ± 0.002 |
| 1.00 | 0.245 ± 0.011 | 0.240 ± 0.006 | 0.220 ± 0.008 |
| 2.00 | 0.216 ± 0.004 | 0.245 ± 0.015 | 0.208 ± 0.003 |
| 5.00 | 0.228 ± 0.007 | 0.239 ± 0.002 | 0.199 ± 0.018 |
| 10.00 | 0.227 ± 0.007 | 0.243 ± 0.005 | 0.227 ± 0.006 |

Thus, it was found that, with respect to the use of any of Triton™ X-100, Triton™ X-114 and Igepal™ CA630, when the surfactant concentration is in the range of from 0.2 to 10.0% (w/v), intrinsic MPO can be released from the white blood cells to a satisfactory extent.

EXAMPLE 3

MPO-releasing Effects of Various Surfactants 10 ml of healthy human whole blood was collected using a 28 G winged intravenous injection needle (manufactured and sold by Terumo Corporation, Japan), and immediately mixed with 10 mg of EDTA-2K (manufactured and sold by Dojin Laboratories, Japan), and the resultant EDTA-containing whole blood sample was subjected to the below-described various measurements within 1 hour from the blood collection.

The myeloperoxidase concentration was measured by the following method.

500 μl of the blood was put in a 2-ml Eppendorf tube, and 500 μl of a 1% (w/v) aqueous surfactant solution was added to the tube, and the resultant mixture was stirred for 2 seconds by a Vortex mixer. Subsequently, the mixture was allowed to stand for 60 minutes on ice to thereby lyze the white blood cells. After the lysis of the white blood cells, 100 μl of the mixture was taken out and added to 900 μl of a PBS solution containing dissolved therein 1% BSA (trade name: "Sigma fraction V", manufactured and sold under the brand of SIGMA™, U.S.A.). The resultant mixture was stirred by a Vortex mixer, and then 10 μl of the mixture was taken out and diluted 2,000-fold with 1% BSA/PBS solution. The resultant diluted mixture was subjected to a measurement by ELISA.

The outline of the ELISA is as follows. A 5 μg/ml PBS solution of an anti-MPO antibody was put into the wells of a Nunc Immuno Plate (manufactured and sold by Nalge Nunc International, Denmark) in an amount of 100 μl per well. The solution in each well was sealed and subjected to a reaction for 18 hours at 4° C. thereby immobilizing the primary antibody. The wells were washed with a washing solution (0.05% Tween™ 20/PBS) and then subjected to blocking for 1 hour at room temperature by using 200 μl of a blocking solution (1% BSA/PBS), and then washed twice with the washing solution. Then, the above-obtained diluted mixture (blood sample which had been treated with a surfactant and then diluted) was put in the wells in an amount of 100 μl per well, and subjected to a reaction for 2 hours at room temperature. Then, the wells were washed 3 times with the washing solution, and a 5 μg/ml solution of an HRP-labeled anti-MPO antibody (an HRP-labeled anti-MPO antibody which was prepared in the same manner as in Example 2) was put in the wells in an amount of 100 μl per well, and subjected to a reaction for 1 hour at room temperature. The wells were washed 5 times with a washing solution, and 100 μl of a just-prepared TMB solution (manufactured and sold by Kirkegaad & Perry Laboratories, U.S.A.) was added thereto to effect a color reaction. 2 Minutes after the start of the color reaction, 100 μl of a 1 N sulfuric acid solution (manufactured and sold by Nacalai Tesque, Inc., Japan) was added to the wells to thereby terminate the reaction. Then, the absorbance at 450 nm was measured by means of a plate reader (manufactured and sold by Bio-Rad Laboratories, U.S.A.).

With respect to the measurement of the MPO concentration of the sample, MPO (manufactured and sold by Elastin Products Co., INC., U.S.A.) was added to the sample so that the final concentration of the added MPO became 5 ng/ml or 10 ng/ml, and the resultant mixture was measured with respect to the MPO concentration. From the obtained value of MPO concentration, a calibration curve for each sample was obtained. The obtained calibration curve was corrected, based on its relationship with a calibration curve obtained with respect to a standard MPO solution, and the corrected calibration curve of each sample was used to determine the MPO concentration of the whole blood. The measurement was conducted 3 times, and a mean value±standard deviation was obtained.

The tested surfactants are as follows:
  Hexadecyltrimethylammonium Bromide (HTAB) (manufactured and sold by Wako Pure Chemical Industries, Ltd., Japan),
  Triton™ X-114 (manufactured and sold by Nacalai Tesque, Inc., Japan),
  Triton™ X-100 (manufactured and sold under the brand of SIGMA™, U.S.A.),
  Triton™ DF-12 (manufactured and sold under the brand of SIGMA™, U.S.A.),
  Brij™ 56 (manufactured and sold under the brand of SIGMA™, U.S.A.),
  Brij™ 97 (manufactured and sold under the brand of SIGMA™, U.S.A.),
  Igepal™ CA630 (manufactured and sold under the brand of SIGMA™, U.S.A.),
  Nissan Nonion NS-208.5 (manufactured and sold by Nippon Oil and Fats Co., Ltd., Japan), and
  Nissan Dispanol TOC (manufactured and sold by Nippon Oil and Fats Co., Ltd., Japan).

These surfactants were individually dissolved in purified water (manufactured and sold by Kyoei Seiyaku Co., Japan) so as to obtain 10% or 2% (w/v) aqueous solutions. Before use in the testing, each of the aqueous solutions was further diluted to obtain a 1% (w/v) aqueous solution, and the 1% (w/v) aqueous solution was used in the testing within 15 hours from the preparation thereof. As a control, purified water (manufactured and sold by Kyoei Seiyaku Co., Japan) was used.

The results are shown in Table 3.

TABLE 3

| Surfactant | MPO concentration of whole blood (μg/ml) |
| --- | --- |
| Triton ™ X-114 | 7.44 ± 1.81 |
| Nissan Dispanol TOC | 7.00 ± 1.64 |
| Triton ™ X-100 | 6.43 ± 1.25 |
| Igepal ™ CA630 | 6.23 ± 1.42 |
| Nissan Nonion NS-208.5 | 6.20 ± 1.51 |
| Brij ™ 97 | 6.08 ± 1.44 |
| Brij ™ 56 | 6.02 ± 1.38 |
| HTAB | 5.80 ± 1.41 |
| Purified water | 2.02 ± 0.87 |

Thus, it was shown that any of the tested surfactants was able to efficiently release intrinsic MPO from the white blood cells contained in a whole blood sample.

EXAMPLE 4

MPO-releasing Effects of Various Surfactants

By the same method as in Example 3, the below-mentioned various surfactants were measured with respect to their effects for releasing MPO from the white blood cells contained in a whole blood sample. The tested surfactants are as follows:
  Hexadecylpyridinium Chloride Monohydrate (HPC),
  Hexadecylpyridinium Bromide Monohydrate (HPB),
  Hexadecyltrimethylammonium Chloride (HTAC),
  n-Dodecyltrimethylammonium Bromide (DTAB),
  Hexadecyltrimethylammonium Bromide (HTAB),
  1-Laurylpyridinium Chloride (LPC), and
  Tetradecyltrimethylammonium Bromide (TTAB) (all of these surfactants are manufactured and sold by Wako Pure Chemical Industries, Ltd., Japan).

These surfactants were individually dissolved in purified water (manufactured and sold by Kyoei Seiyaku Co., Japan) so as to obtain 10% or 2% (w/v) aqueous solutions. Before use in the testing, each of the aqueous solutions was further diluted to obtain a 1% (w/v) aqueous solution, and the 1%

(w/v) aqueous solution was used in the testing within 15 hours from the preparation thereof. As a control, purified water (manufactured and sold by Kyoei Seiyaku Co., Japan) was used. The results are shown in Table 4.

TABLE 4

| Surfactant | MPO concentration of whole blood ($\mu$g/ml) |
|---|---|
| HPC | 12.05 ± 1.18 |
| HPB | 10.96 ± 0.46 |
| HTAC | 10.93 ± 0.82 |
| DTAC | 9.95 ± 0.71 |
| HTAB | 9.58 ± 0.53 |
| LPC | 9.58 ± 1.39 |
| TTAB | 9.33 ± 1.30 |
| Purified water | 1.65 ± 0.81 |

Thus, it was shown that any of the tested cationic surfactants was able to satisfactorily release intrinsic MPO from the white blood cells contained in a whole blood sample.

EXAMPLE 5

MPO-releasing Effects of Various Surfactants

By the same method as in Example 3, the below-mentioned various surfactants were measured with respect to their effects for releasing MPO from the white blood cells contained in a whole blood sample. The tested surfactants are as follows:

Hexadecylpyridinium Chloride Monohydrate (HPC),
Hexadecylpyridinium Bromide Monohydrate (HPB),
Hexadecyltrimethylammonium Chloride (HTAC),
n-Dodecyltrimethylammonium Bromide (DTAB),
Hexadecyltrimethylammonium Bromide (HTAB),
1-Laurylpyridinium Chloride (LPC),
Tetradecyltrimethylammonium Bromide (TTAB) (wherein all of the above-mentioned surfactants are manufactured and sold by Wako Pure Chemical Industries, Ltd., Japan),
Didecyldimethylammonium Chloride (DDAC), and
Octadecyltrimethylammonium Chloride (OTAC) (wherein the last two surfactants are manufactured and sold by Nippon Oil and Fats Co., Ltd., Japan).

These surfactants were individually dissolved in purified water (manufactured and sold by Kyoei Seiyaku Co., Japan) so as to obtain 10% or 2% (w/v) aqueous solutions. Before use in the testing, each of the aqueous solutions was further diluted to obtain a 1% (w/v) aqueous solution, and the 1% (w/v) aqueous solution was used in the testing within 15 hours from the preparation thereof. As a control, purified water (manufactured and sold by Kyoei Seiyaku Co., Japan) was used. The results are shown in Table 5.

TABLE 5

| Surfactant | MPO concentration of whole blood ($\mu$g/ml) |
|---|---|
| HPC | 10.60 ± 1.44 |
| DTAC | 9.28 ± 0.60 |
| HPB | 9.07 ± 1.14 |
| TTAB | 8.08 ± 0.11 |
| DTAB | 8.05 ± 0.64 |
| DTAC | 7.88 ± 0.46 |

TABLE 5-continued

| Surfactant | MPO concentration of whole blood ($\mu$g/ml) |
|---|---|
| LPC | 7.57 ± 0.60 |
| OTAC | 7.47 ± 0.38 |
| HTAC | 7.35 ± 0.28 |
| HTAB | 7.15 ± 2.69 |
| Purified water | 1.58 ± 0.97 |

Thus, it was shown that any of the tested cationic surfactants was able to satisfactorily release intrinsic MPO from the white blood cells contained in a whole blood sample.

EXAMPLE 6

Relationship Between the Release Amount of MPO and the HLB Value of the Surfactant Blood collection, treatment with a surfactant, and ELISA were performed in the same manner as in Example 3 in order to measure the MPO-releasing effects of the below-mentioned various surfactants.

The tested surfactants are the following nonionic surfactants:

Nonidet™-P40 (manufactured and sold by Nacalai Tesque, Inc., Japan),
Triton™ X-114 (manufactured and sold by Nacalai Tesque, Inc., Japan),
Triton™ X-100 (manufactured and sold under the brand of SIGMA™, U.S.A.),
Triton™ X-207 (manufactured and sold under the brand of SIGMA™, U.S.A.),
Triton™ X-305 (manufactured and sold under the brand of SIGMA™, U.S.A.),
Brij™ 35 (manufactured and sold under the brand of SIGMA™, U.S.A.),
Brij™ 56 (manufactured and sold under the brand of SIGMA™, U.S.A.),
Brij™ 58 (manufactured and sold under the brand of SIGMA™, U.S.A.),
Brij™ 97 (manufactured and sold under the brand of SIGMA™, U.S.A.),
Brij™ 98 (manufactured and sold under the brand of SIGMA™, U.S.A.),
Igepal™ CA630 (manufactured and sold under the brand of SIGMA™, U.S.A.),
Tween™ 65 (manufactured and sold under the brand of SIGMA™, U.S.A.),
Tween™ 85 (manufactured and sold under the brand of SIGMA™, U.S.A.),
Tween™ 20 (manufactured and sold by Bio-Rad Laboratories, U.S.A.), and
Triton™ X-45 (manufactured and sold by Fluka, Switzerland).

These surfactants were individually dissolved in purified water (manufactured and sold by Kyoei Seiyaku Co., Japan) so as to obtain 10% or 2% (w/v) aqueous solutions. Before use in the testing, each of the aqueous solutions was further diluted to obtain a 1% (w/v) aqueous solution, and the 1% (w/v) aqueous solution was used in the testing within 15 hours from the preparation thereof. As a control, purified water (manufactured and sold by Kyoei Seiyaku Co., Japan) was used.

As shown in FIG. 1, it was found that the release amount of MPO from the white blood cells in whole blood which has been treated with a surfactant varies, depending on the HLB value of the surfactant and that the use of a surfactant having an HLB value of from 12 to 14 is suitable for releasing MPO from the white blood cells.

EXAMPLE 7 AND COMPARATIVE EXAMPLES 1 AND 2

Relationship Between Each of Myeloperoxidase, Lactoferrin and Elastase and Each of White Blood Cell Count and Neutrophil Count In Example 7 and Comparative Examples 1 and 2, there were used whole blood samples (Group A) obtained from 13 healthy humans, and whole blood samples (Group B) obtained from 14 non-healthy humans who were known to have specific diseases. 10 ml of each whole blood sample was put in a test tube containing 10 mg of EDTA-2K (manufactured and sold by Dojin Laboratories, Japan) and the resultant EDTA-containing whole blood sample was stirred well. A portion of the obtained EDTA-containing whole blood sample was taken out and subjected to the determination of a white blood cell count and a neutrophil count by means of CELL-DYNE™ 3500 (manufactured and sold by DAINABOT, U.S.A.). Further, 1 ml of the EDTA-containing whole blood sample was taken out, and 100 μl of an aqueous 11% (w/v) solution of Triton™ X-100 (manufactured and sold under the brand of SIGMA™, U.S.A.) was added to the taken-out 1 ml whole blood sample, and the resultant mixture was stirred well and then allowed to stand at room temperature for 1 hour to thereby lyze the white blood cells contained in the whole blood to obtain a (whole blood sample/surfactant) mixture containing the lyzed white blood cells.

(1) Measurement of Myeloperoxidase (Example 7)

The myeloperoxidase (MPO) concentration was measured as follows. The above-mentioned (whole blood sample/surfactant) mixture containing the lyzed white blood cells was diluted 2,000-fold with a sample diluting buffer (20 mM phosphate buffer (pH 7.4) containing 0.1% bovine serum albumin and 0.2% sodium azide), which buffer is attached to BIOXYTEC™ MPO Enzyme Immunoassay kit (manufactured and sold by OXIS International, Inc., U.S.A.), and the resultant diluted mixture was taken as a sample for the measurement of myeloperoxidase (MPO).

With respect to the above-mentioned sample for the measurement of MPO and a standard MPO solution (which is obtained by dissolving commercially available MPO in the above mentioned buffer), the measurement of the MPO concentration was performed using BIOXYTEC™ MPO Enzyme Immunoassay kit (manufactured and sold by OXIS International, Inc., U.S.A.) in accordance with the instrucction manual attached thereto. Specifically, with respect to the measurement of the MPO concentration of the above-mentioned sample, MPO (manufactured and sold by Elastin Products Co., INC., U.S.A.) was added to the sample so that the final concentration of the added MPO became 5 ng/ml or 10 ng/ml, and the resultant mixture was measured with respect to the MPO concentration. From the obtained value of MPO concentration, a calibration curve for each sample was obtained. The obtained calibration curve was corrected, based on its relationship with a calibration curve obtained with respect to the standard MPO solution, and the corrected calibration curve of each sample was used to determine the MPO concentration of the whole blood. The measurement was conducted 3 times, and a mean value was obtained.

(2) Measurement of Lactoferrin (Comparative Example 1)

The lactoferrin (LTF) concentration was measured as follows. The above-mentioned (whole blood sample/surfactant) mixture containing the lyzed white blood cells was diluted 2,000-fold with a sample diluting buffer (20 mM phosphate buffer (pH 7.4) containing 150 mM NaCl, 2 mg/ml bovine serum albumin, 0.1% Tween™ 20 and 0.01% merthiolate), which buffer is attached to BIOXYTEC™ Lactof Enzyme Immunoassay kit (manufactured and sold by OXIS International, Inc., U.S.A.), and the resultant diluted mixture was taken as a sample for the measurement of lactoferrin (LTF).

With respect to the above-mentioned sample for the measurement of LTF and a standard LTF solution (which is obtained by dissolving commercially available LTF in the above mentioned buffer), the measurement of the LTF concentration was performed using BIOXYTEC™ Lactof Enzyme Immunoassay kit (manufactured and sold by OXIS International, Inc., U.S.A.) in accordance with the instruction manual attached thereto. Specifically, with respect to the measurement of the LTF concentration of the above-mentioned sample, LTF (manufactured and sold by ICN Pharmaceuticals, Inc., U.S.A.) was added to the sample so that the final concentration of the added LTF became 5 ng/ml or 10 ng/ml, and the resultant mixture was measured with respect to the LTF concentration. From the obtained value of LTF concentration, a calibration curve for each sample was obtained. The obtained calibration curve was corrected, based on its relationship with a calibration curve obtained with respect to the standard LTF solution, and the corrected calibration curve of each sample was used to determine the LTF concentration of the whole blood. The measurement was conducted 3 times, and a mean value was obtained.

(3) Measurement of Elastase (Comparative Example 2)

The elastase (ELT) concentration was measured as follows. The above-mentioned (whole blood sample/surfactant) mixture containing the lyzed white blood cells was diluted 2,000-fold with a sample diluting buffer (20 mM phosphate buffer (pH 7.4) containing 0.1% bovine serum albumin and 0.2% sodium azide), which buffer is attached to PMN Elastase kit (manufactured and sold by MERCK, U.S.A.), and the resultant diluted mixture was taken as a sample for the measurement of elastase (ELT).

With respect to the above-mentioned sample for the measurement of ELT and a standard ELT solution (which is obtained by dissolving commercially available ELT in the above-mentioned buffer), the measurement of the ELT concentration was performed using PMN Elastase kit (manufactured and sold by MERCK, U.S.A.) in accordance with the instruction manual attached thereto. Specifically, with respect to the measurement of the ELT concentration of the above-mentioned sample, ELT attached to the kit was added to the sample so that the final concentration of the added ELT became 5 ng/ml or 10 ng/ml, and the resultant mixture was measured with respect to the ELT concentration. From the obtained value of ELT concentration, a calibration curve was obtained. The obtained calibration curve was corrected, based on its relationship with a calibration curve obtained with respect to the standard ELT solution, and the corrected calibration curve of each sample was used to determine the ELT concentration of the whole blood. The measurement was conducted 3 times, and a mean value was obtained.

The results of Example 7 and Comparative Examples 1 and 2 (concentrations of MPO, LTF and ELT in healthy human whole blood and non-healthy human whole blood) are shown in Table 6 together with the white blood cell count and the neutrophil count of the blood.

TABLE 6

| Sample No. | White blood cell count (cells/μl) | Neutrophil count (cells/μl) | Example 7 MPO concentration (μg/ml) | Comparative Example 1 LTF concentration (μg/ml) | Comparative Example 2 ELT concentration (μg/ml) | Name of disease |
|---|---|---|---|---|---|---|
| colspan="7" | Group A: healthy human whole blood |||||||
| 1. | 2600 | 1100 | 6.08 | 4.22 | 3.64 | — |
| 2. | 3100 | 1000 | 4.60 | 5.32 | 3.12 | |
| 3. | 5400 | 2300 | 9.72 | 7.69 | 6.73 | |
| 4. | 7600 | 4900 | 16.02 | 14.54 | 14.79 | |
| 5. | 2700 | 1100 | 4.77 | 3.77 | 3.62 | |
| 6. | 6900 | 4100 | 12.85 | 8.99 | 10.75 | |
| 7. | 4600 | 2400 | 9.72 | 5.75 | 9.46 | |
| 8. | 7700 | 5400 | 14.01 | 15.74 | 10.45 | |
| 9. | 3200 | 1400 | 7.75 | 5.70 | 3.91 | |
| 10. | 5100 | 2300 | 11.02 | 5.30 | 6.20 | |
| 11. | 4800 | 1800 | 8.56 | 5.81 | 4.92 | |
| 12. | 6100 | 3800 | 15.49 | 9.55 | 10.79 | |
| 13. | 7100 | 3700 | 16.37 | 5.71 | 7.95 | |
| colspan="7" | Group B: non-healthy human whole blood |||||||
| 1. | 13000 | 10400 | 25.99 | 15.17 | 16.22 | cirrhosis, metastatic cancer of the liver |
| 2. | 11000 | 6600 | 19.10 | 18.20 | 13.44 | diabetes |
| 3. | 13300 | 11000 | 38.87 | 28.51 | 31.13 | cirrhosis, hepatoma |
| 4. | 11100 | 8600 | 20.28 | 28.30 | 21.64 | intrapelvic tumor, partial excision of large and small intestines |
| 5. | 19900 | 18900 | 51.70 | 37.17 | 109.21 | obstructive jaundice, acute pancreatitis, acute cholecystitis |
| 6. | 23500 | 20500 | 31.17 | 41.66 | 56.65 | bronchial asthma |
| 7. | 12000 | 10100 | 29.06 | 13.83 | 44.83 | obstructive jaundice, acute pancreatitis, acute cholecystitis |
| 8. | 13900 | 11100 | 18.08 | 22.26 | 28.66 | gallstone disease, cholecystitis |
| 9. | 18000 | 16300 | 39.35 | 19.70 | 46.18 | large bowel cancer, ileus |
| 10. | 19700 | 18300 | 45.67 | 23.74 | 32.94 | choledocholithiasis, obstructive jaundice |
| 11. | 16100 | 14600 | 19.62 | 36.11 | 50.93 | hepatoma |
| 12. | 14400 | 13700 | 21.41 | 18.46 | 79.88 | ileus, large bowel cancer |
| 13. | 15900 | 14500 | 28.52 | 33.48 | 29.45 | intrapelvic tumor, partial excision of large and small intestines |
| 14. | 27000 | 25800 | 54.64 | 22.08 | 66.87 | large bowel cancer, ileus |

Figure 2A:
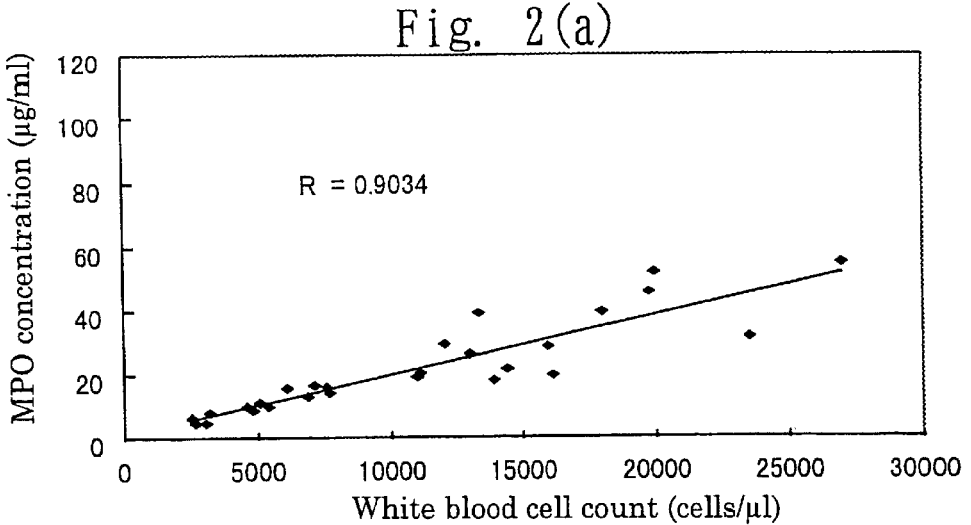
FIG. 2(a) is a diagram showing the correlation between the MPO concentrations of whole blood samples obtained from healthy and non-healthy humans and the white blood cell counts of the whole blood samples.
Figure 2B:
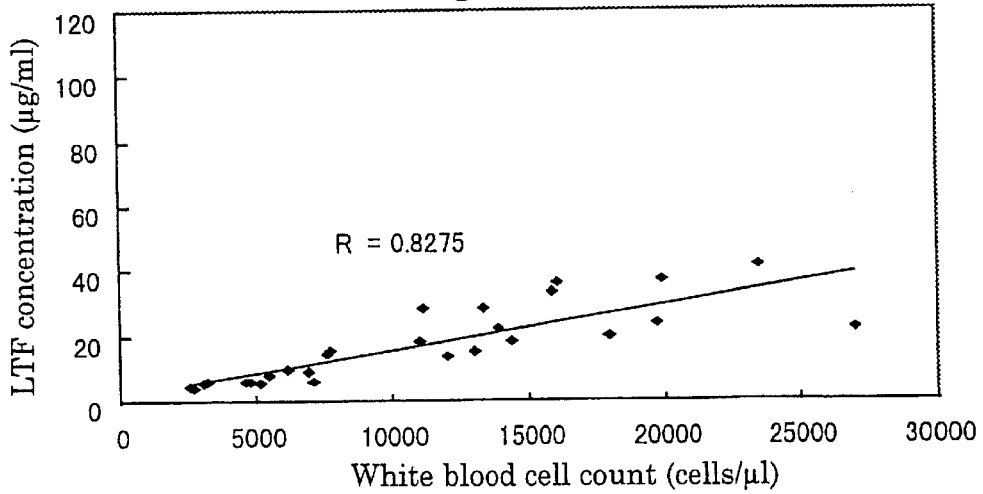
FIG. 2(b) is a diagram showing the correlation between the lactoferrin (LTF) concentrations of whole blood samples obtained from healthy and non-healthy humans and the white blood cell counts of the whole blood samples.
Figure 2C:
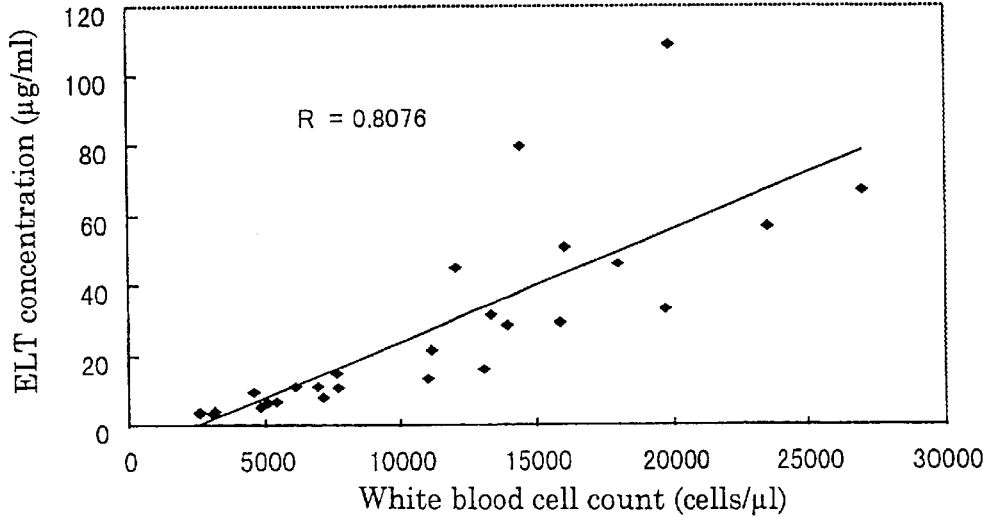
FIG. 2(c) is a diagram showing the correlation between the elastase (ELT) concentrations of whole blood samples obtained from healthy and non-healthy humans and the white blood cell counts of the whole blood samples.
Figure 3A:
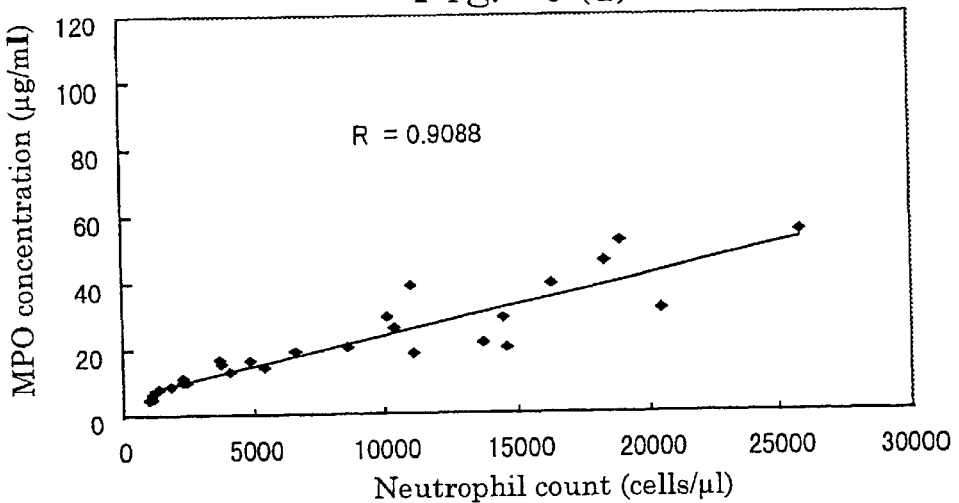
FIG. 3(a) is a diagram showing the correlation between the MPO concentrations of whole blood samples obtained from healthy and non-healthy humans and the neutrophil counts of the whole blood samples.
Figure 3B:
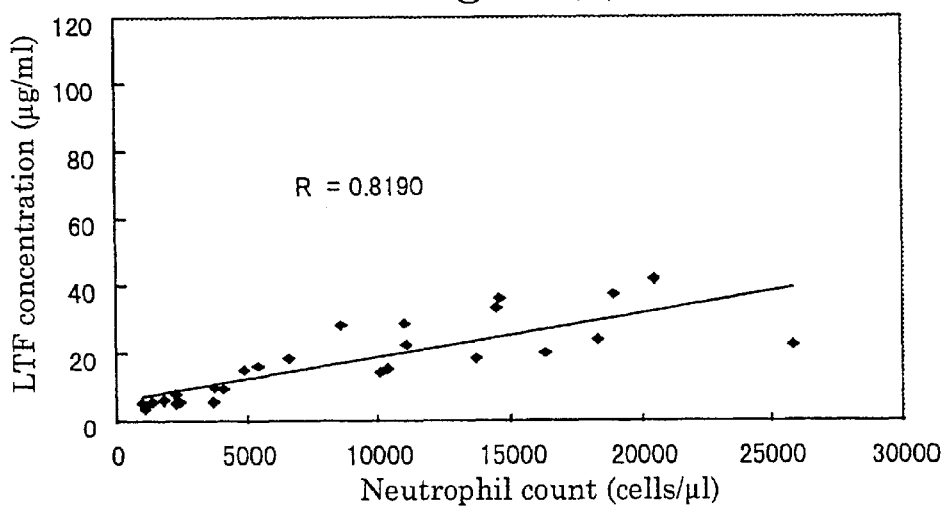
FIG. 3 (b) is a diagram showing the correlation between the LTF concentrations of whole blood samples obtained from healthy and non-healthy humans and the neutrophil counts of the whole blood samples.
FIG. 3(c) is a diagram showing the correlation between the ELT concentrations of whole blood samples obtained from healthy and non-healthy humans and the neutrophil counts of the whole blood samples.
Figure 3C:
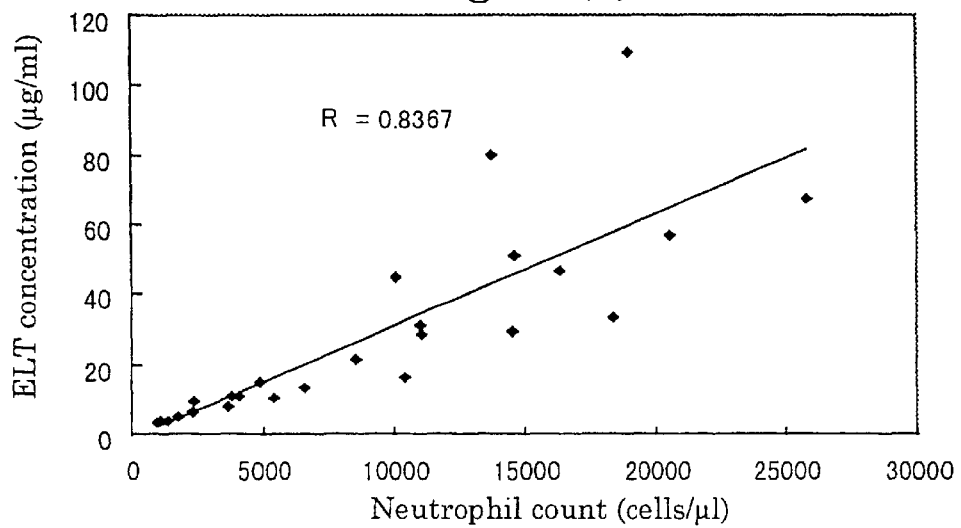
Figure 4A:
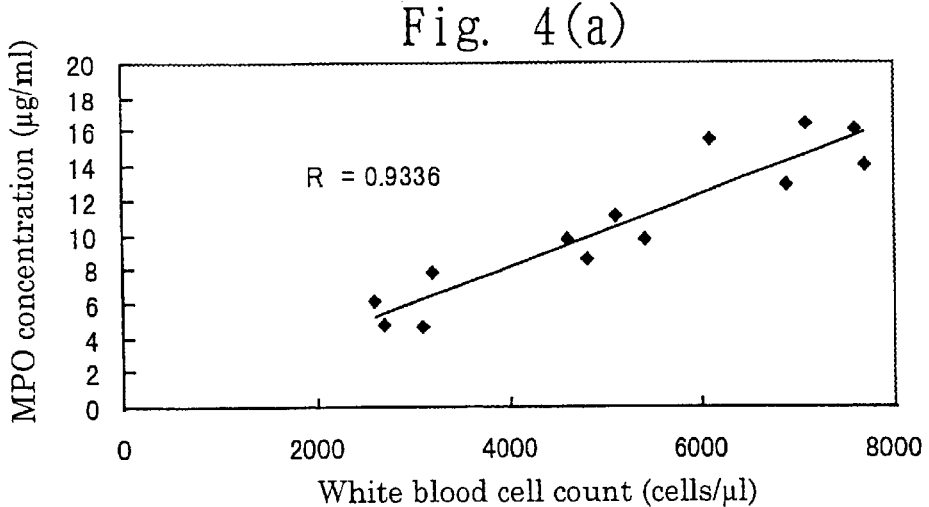
FIG. 4(a) is a diagram showing the correlation between the MPO concentrations of whole blood samples obtained from healthy humans and the white blood cell counts of the whole blood samples.
Figure 4B:
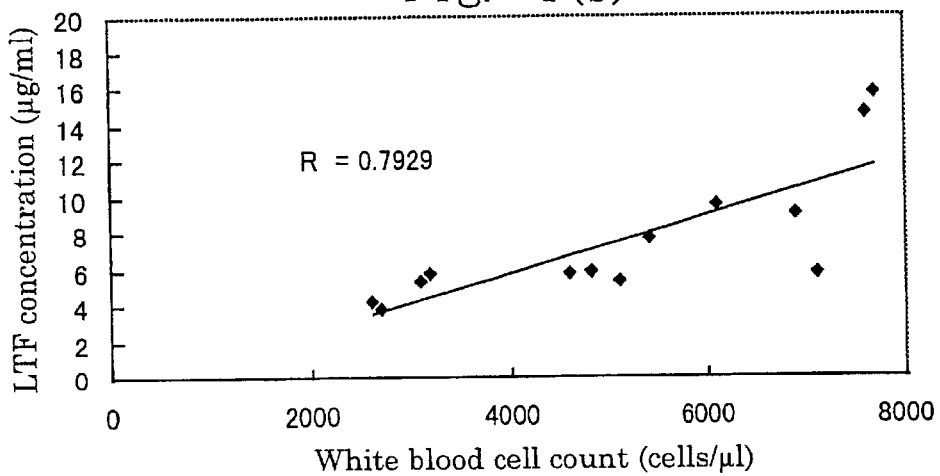
FIG. 4(b) is a diagram showing the correlation between the LTF concentrations of whole blood samples obtained from healthy humans and the white blood cell counts of the whole blood samples.
Figure 4C:
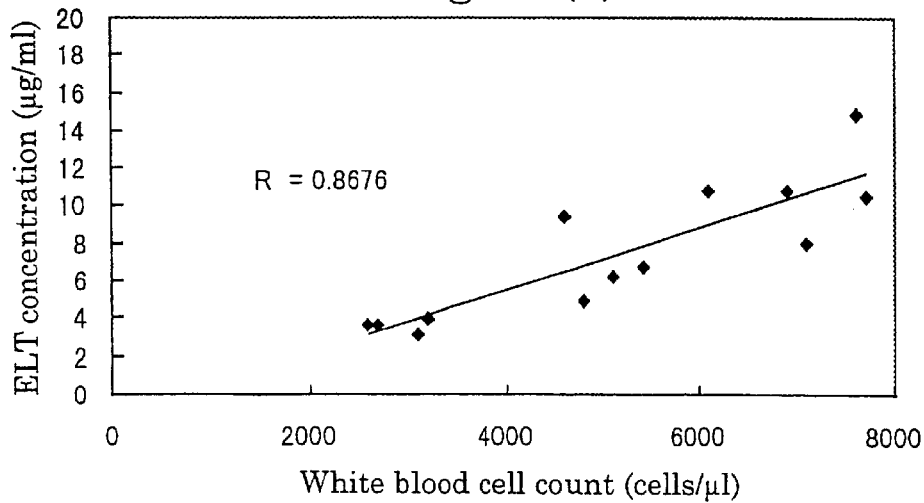
FIG. 4(c) is a diagram showing the correlation between the ELT concentrations of whole blood samples obtained from healthy humans and the white blood cell counts of the whole blood samples.
Figure 5A:
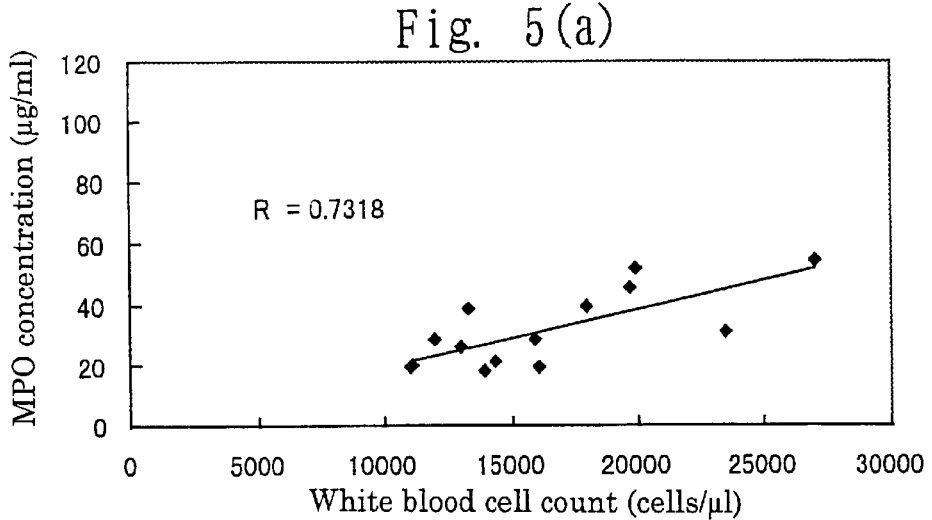
FIG. 5(a) is a diagram showing the correlation between the MPO concentrations of whole blood samples obtained from non-healthy humans and the white blood cell counts of the whole blood samples.
Figure 5B:
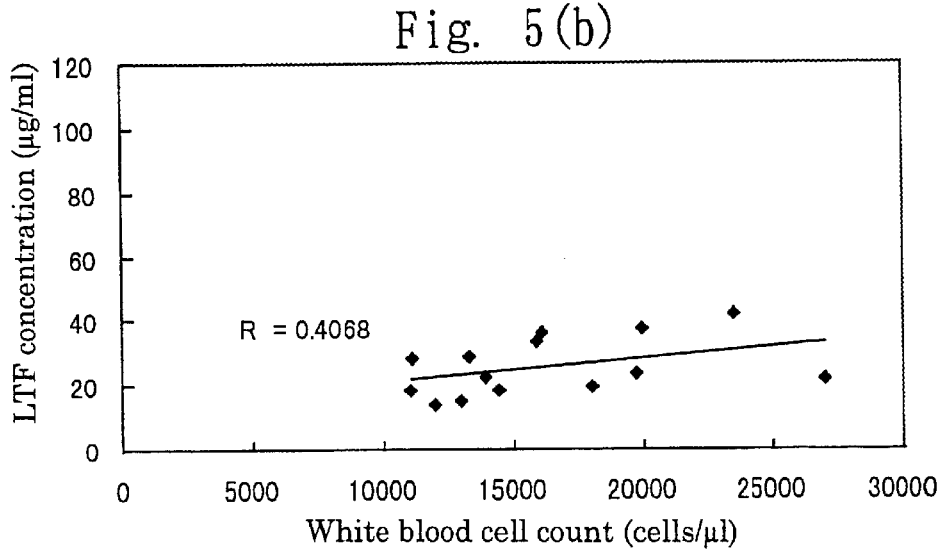
FIG. 5(b) is a diagram showing the correlation between the LTF concentrations of whole blood samples obtained from non-healthy humans and the white blood cell counts of the whole blood samples.
Figure 5C:
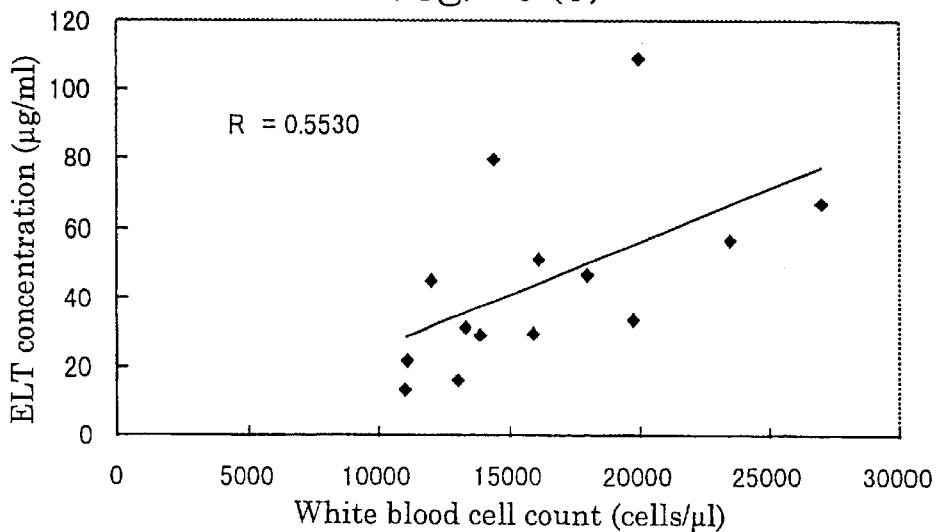
FIG. 5(c) is a diagram showing the correlation between the ELT concentrations of whole blood samples obtained from non-healthy humans and the white blood cell counts of the whole blood samples.

Further, based on all results of the measurements concerning both the healthy human whole blood samples (Group A) and the non-healthy human whole blood samples (Group B), the correlations between the white blood cell counts and the concentrations of the intrinsic substances (MPO, LTF and ELT) were examined and the results are shown in FIGS. 2(a) to 2(c). Also, the correlations between the neutrophil counts and the concentrations of the intrinsic substances (MPO, LTF and ELT) were examined and the results are shown in FIGS. 3(a) to 3(c).

As shown in FIGS. 2(a) to 2(c) and FIGS. 3(a) to 3(c), the below-described correlations were found between the concentrations of the intrinsic substances (MPO, LTF and ELT) and the white blood cell counts as well as the neutrophil counts.

The regression function showing the correlation between the MPO concentration (y) and the white blood cell count (x) is as follows:

$$y=0.0019x+0.6981 \ (R=0.9034).$$

(As mentioned above, R represents the correlation coefficient. This applies to all R's mentioned below.)

The regression function showing the correlation between the MPO concentration (y) and the neutrophil count (x) is as follows:

$$y=0.0018x+5.5395 \ (R=0.9088).$$

The regression function showing the correlation between the LTF concentration (y) and the white blood cell count (x) is as follows:

$$y=0.0014x+1.6278 \ (R=0.8275).$$

The regression function showing the correlation between the LTF concentration (y) and the neutrophil count (x) is as follows:

$$y=0.0013x+5.3757 \ (R=0.8190).$$

The regression function showing the correlation between the ELT concentration (y) and the white blood cell count (x) is as follows:

$$y=0.0032x-8.4464 \ (R=0.8076).$$

The regression function showing the correlation between the ELT concentration (y) and the neutrophil count (x) is as follows:

$$y=0.0032x-1.0451 \ (R=0.8367).$$

Thus, it was shown that each of the white blood cell count and the neutrophil count exhibited a close correlation with the MPO concentration.

EXAMPLE 8 AND COMPARATIVE EXAMPLES 3 AND 4

Analysis of the Correlation Between Each of the MPO, LTF and ELT Concentrations and the White Blood Cell Count with Respect to Each of the Group of the Healthy Human Whole Blood Samples and the Group of the Non-healthy Human Whole Blood Samples The data obtained in Example 7 and Comparative Examples 1 and 2 were separated into the data of the healthy human whole blood samples (Group A) each having a white blood cell count of less than 10,000 cells/μl and the data of the non-healthy human whole blood samples (Group B) each having a white blood cell count of 10,000 cells/μl or more. With respect to each of the data of Group A and the data of Group B, the correlation between each of the MPO, LTF and ELT concentrations and the white blood cell count was analyzed. The results are shown in FIGS. 4(a) to 4(c) and FIGS. 5(a) to 5(c).

The analysis of the data of Group A (healthy human whole blood samples) showed that, with respect to Group A, the correlation coefficient (R) of the relationship between the MPO concentration and the white blood cell count was extremely high, specifically R=0.9336 (y=0.0021x−0.2414), as compared to any of the correlation coefficient (R) of the relationship between the LTF concentration and the white blood cell count (R=0.7929; y=0.0016x−0.7488) and the correlation coefficient (R) of the relationship between the ELT concentration and the white blood cell count (R=0.8676; y=0.0017x−1.33). Therefore, it was found that, in the case of healthy human whole blood samples, most accurate determination of a white blood cell count can be obtained by measuring the MPO concentration.

Also, the analysis of the data of Group B (non-healthy human whole blood samples) showed that, with respect to Group B, the correlation coefficient (R) of the relationship between the MPO concentration and the white blood cell count was high, specifically R=0.7318, as compared to any of the correlation coefficient (R) of the relationship between the LTF concentration and the white blood cell count and the correlation coefficient (R) of the relationship between the ELT concentration and the white blood cell count. Further, with respect to the data of Group B, attention was paid to the gradient of a regression line showing the correlation between each of the MPO, LTF and ELT concentrations and the white blood cell count. The gradients of the regression lines of the MPO, LTF and ELT concentrations versus the white blood cell count in Group B were, respectively, compared to the gradients of the regression lines of the MPO, LTF and ELT concentrations versus the white blood cell count in Group A. The comparison showed the following. The gradient of the regression line showing the correlation between the MPO concentration and the white blood cell count in Group B was 0.0019 (y=0.0019x+0.5678), which is close to the gradient (0.0021) of the regression line showing the correlation between the MPO concentration and the white blood cell count in Group A. To the contrary, the gradient of the regression line showing the correlation between the LTF concentration and the white blood cell count in Group B was 0.0007 (y=0.0007x+13.447), in contrast to 0.0016 which is the gradient of the regression line showing the correlation between the LTF concentration and the white blood cell count in Group A, that is, it was shown that, in the case of LTF, the gradient of the regression line obtained with respect to Group B was as small as about 1/2.3 of the gradient of the regression line obtained with respect to Group A. Further, the gradient of the regression line showing the correlation between the ELT concentration and the white blood cell count in Group B was 0.0031 (y=0.0031x−5.4788), in contrast to 0.0017 which is the gradient of the regression line showing the correlation between the ELT concentration and the white blood cell count in Group A, that is, it was shown that, in the case of ELT, the gradient of the regression line obtained with respect to Group B was as large as about 1.8 times the gradient of the regression line obtained with respect to Group A. In addition, it was also found that, in the case of a whole blood sample obtained from a patient suffering from obstructive jaundice, acute pancreatitis and acute cholecystitis, the ELT concentration was extremely higher than the concentrations of MPO and LTF, and the ELT concentration exhibited a great deviation from a regression line showing the correlation between the ELT concentration and the white blood cell count in whole blood.

Therefore, it was found that, also in the case of non-healthy human whole blood samples, most accurate determination of a white blood cell count can be obtained by measuring the MPO concentration.

EXAMPLE 9

Correlation Between the MPO Concentration and Each of the White Blood Cell Count and the Neutrophil Count in Human Whole Blood Samples Including Those Having a White Blood Cell Count of 10,000 Cells/μl or More Tests were performed on 46 whole blood samples obtained from outpatients. As a surfactant for lyzing the white blood cells, Triton™ X-100, Triton™ X-114 and Igepal™ CA630 were individually used. A whole blood sample was treated with a surfactant in the same manner as in Example 1, and the MPO concentration was measured in the same manner as in Example 2. The white blood cell count and the neutrophil count were determined by means of Coulter GEN'S System (manufactured and sold by COULTER ELECTRONICS, INC., U.S.A.), and the correlation coefficient of the relationship between the MPO concentration and each of the white blood cell count and the neutrophil count was obtained. The measurement was conducted 3 times, and a mean value±standard deviation was obtained.

Figure 6:
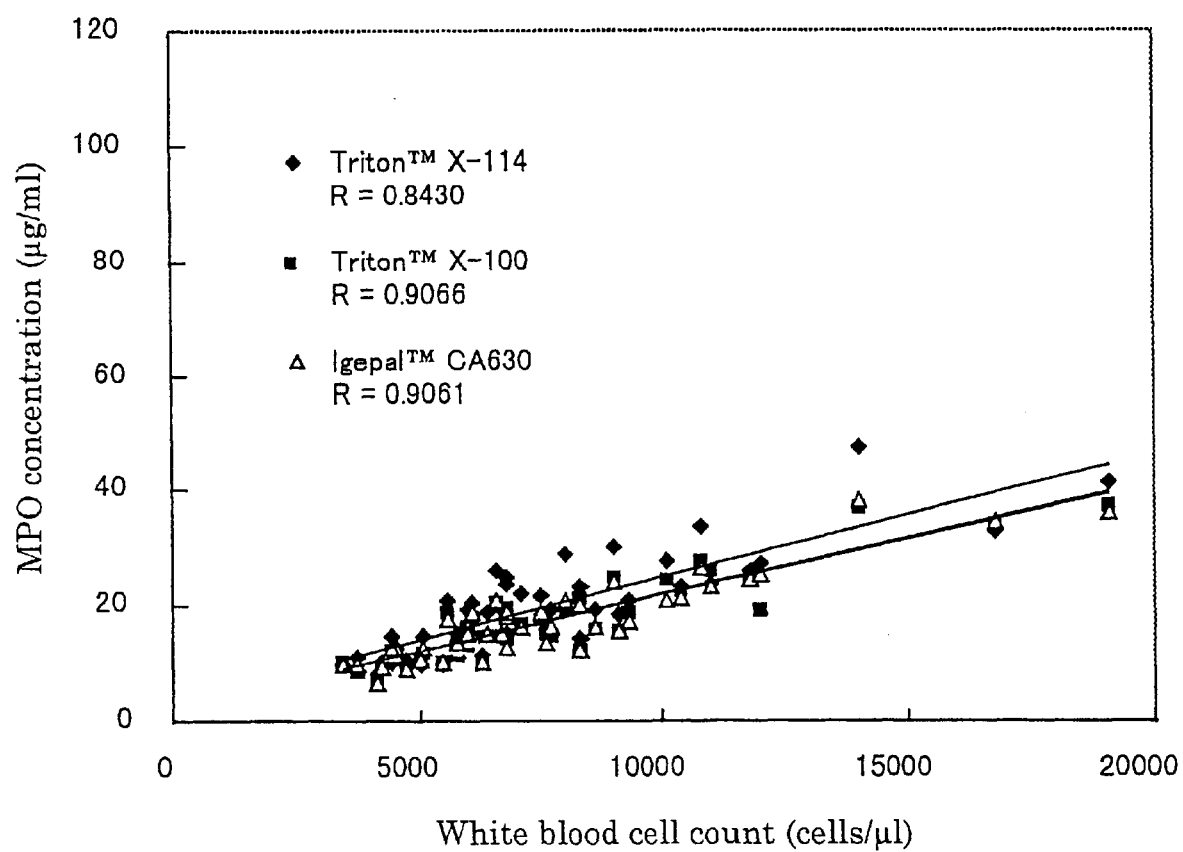
FIG. 6 is a diagram showing the correlation between the MPO concentrations of whole blood samples in cluding those having a white blood cell count of 10,000 cells/$\mu$l or more and the white blood cell counts of the whole blood samples.

The results concerning the white blood cell count are shown in FIG. 6. In the case of the use of Triton™ X-114, the correlation coefficient (R) of the relationship between the MPO concentration and the white blood cell count was R=0.8430 ($p<0.0001$) (y=0.0022x+3.324). In the case of the use of Triton™ X-100, the correlation coefficient (R) of the relationship between the MPO concentration and the white blood cell count was R=0.9066 ($p<0.0001$) (y=0.002x+2.1757). In the case of the use of Igepal™ CA630, the correlation coefficient (R) of the relationship between the MPO concentration and the white blood cell count was R=0.9061 ($p<0.0001$) (y=0.0019x+2.4259). Thus, a very good correlation was found between the MPO concentration and the white blood cell count. Therefore, it was found that, in the case of the human whole blood samples including those having a white blood cell count of 10,000 cells/μl or more, the MPO concentration can be used as an accurate index of the white blood cell count.

Figure 7:
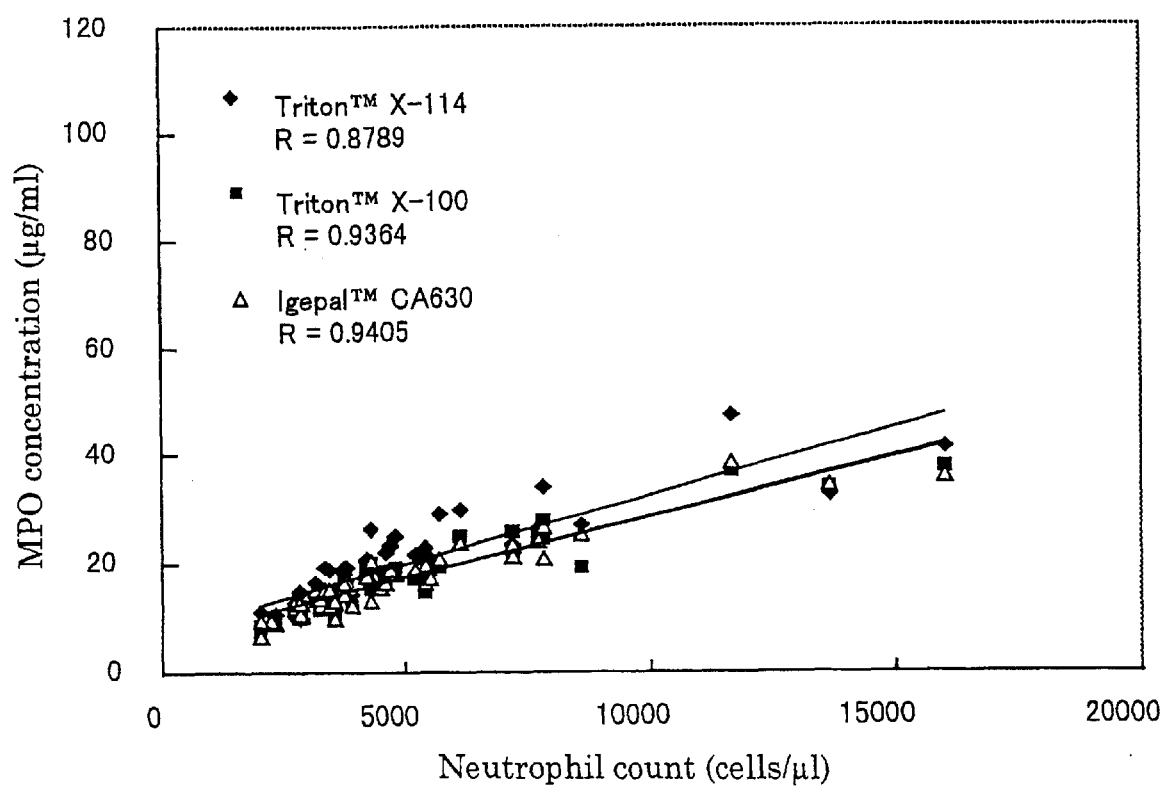
FIG. 7 is a diagram showing the correlation between the MPO concentrations of whole blood samples including those having a white blood cell count of 10,000 cells/$\mu$l or more and the neutrophil counts of the whole blood samples.

The correlation between the MPO concentration and the neutrophil count is shown in FIG. 7. In the case of the use of Triton™ X-114, the correlation coefficient (R) of the relationship between the MPO concentration and the neutrophil count was R=0.8789 ($p<0.0001$) (y=0.0025x+7.4089). In the case of the use of Triton™ X-100, the correlation coefficient (R) of the relationship between the MPO concentration and the neutrophil count was R=0.9364 ($p<0.0001$)(y=0.0023x+5.9748). In the case of the use of Igepal™ CA630, the correlation coefficient (R) of the relationship between the MPO concentration and the neutrophil count was R=0.9405 ($p<0.0001$) (y=0.0022x+6.0951). Thus, a very good correlation was found between the MPO concentration and the neutrophil count, and it is noted that, when these results are compared to the results of the white blood cell count and when the comparison is made with respect to the same surfactant, the correlation between the MPO concentration and the neutrophil count was higher than the correlation between the MPO concentration and the white blood cell count. Therefore, as shown in FIG. 7, it was found that, in the case of the human whole blood samples including those having a white blood cell count of 10,000 cells/µl or more, the MPO concentration can be used as an accurate index of the neutrophil count.

EXAMPLE 10

Correlation Between the White Blood Cell Count/ neutrophil Count as Determined Based on the MPO Concentration and the White Blood Cell Count/ neutrophil Count as Determined by Means of a Blood Cell Counting Apparatus Tests were performed on 46 whole blood samples obtained from outpatients, which samples were the same as co in Example 9. As a surfactant for lyzing the white blood cells, Triton™ X-100 was used. The MPO concentration was measured in the same manner as in Example 2. The obtained MPO concentration was substituted in the regression function obtained in Example 7 which function shows the correlation between the MPO concentration and the white blood cell count, i.e., the function: $y=0.0019x+0.6981$ (see FIG. 2(a)), thereby obtaining a white blood cell count. Also, a white blood cell count was determined by means of a blood cell counting apparatus, specifically Coulter GEN·S System (manufactured and sold by COULTER ELECTRONICS, INC., U.S.A.). The correlation between the white blood cell count as determined based on the MPO concentration and the white blood cell count as determined by means of the blood cell counting apparatus is shown in FIG. 8(a).

Figure 8A:
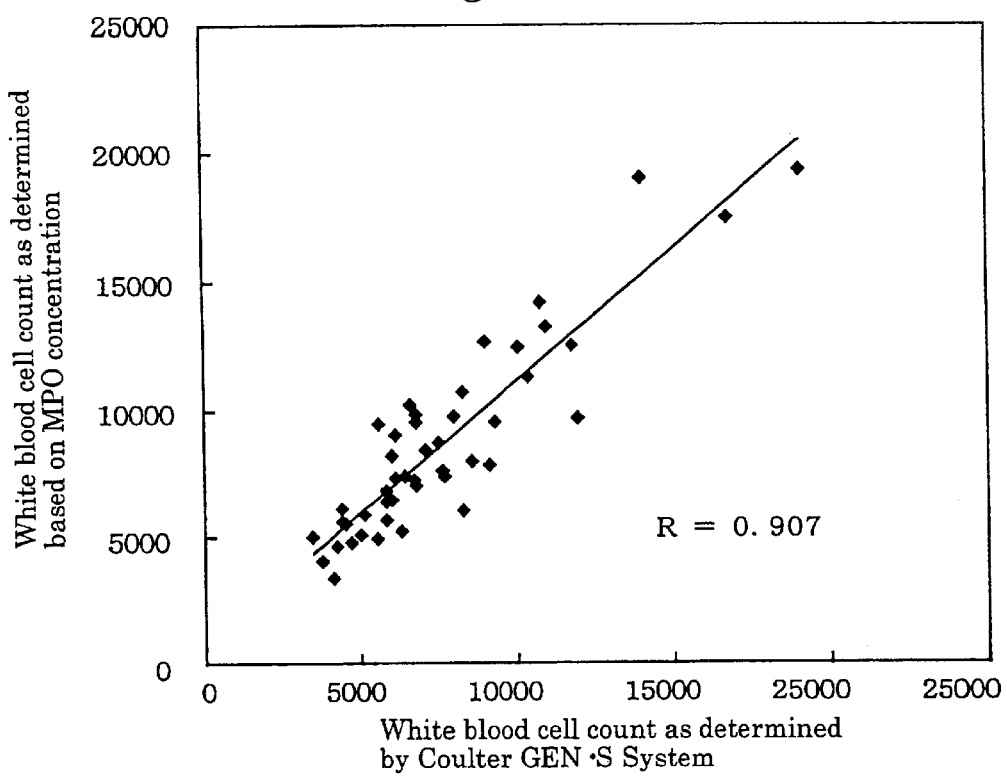
FIG. 8(a) is a diagram showing the correlation between the white blood cell counts as determined based on the MPO concentrations and the white blood cell counts as determined by a blood cell counting apparatus.

As apparent from FIG. 8(a), it was confirmed that, even in the case of the human whole blood samples including those having a white blood cell count of 10,000 cells/µl or more, there is a good correlation ($y=1.0333x+777.69$; $R=0.907$) between the white blood cell count as determined by the method of the present invention and the white blood cell count as determined by means of a blood cell counting apparatus. Therefore, by previously preparing a regression line showing the correlation between the MPO concentration and the white blood cell count in whole blood, a white blood cell count of a whole blood sample can be obtained simply by measuring the MPO concentration of the whole blood sample, wherein the obtained white blood cell count exhibits a good correlation with a white blood cell count as determined by means of a blood cell counting apparatus. Thus, by the method of the present invention, accurate determination of a white blood cell count of a whole blood sample can be easily performed, even in the case of the whole blood samples including those having a white blood cell count of 10,000 cells/µl or more.

Further, the above-obtained MPO concentration was also substituted in the regression function obtained in Example 7 which function shows the correlation between the MPO concentration and the neutrophil count, i.e., the function: $y=0.0018x+5.5395$ (see FIG. 3(a)), thereby obtaining a neutrophil count. Also, a neutrophil count was determined by means of the blood cell counting apparatus, i.e., Coulter GEN·S System (manufactured and sold by COULTER ELECTRONICS, INC., U.S.A.). The correlation between the neutrophil count as determined based on the MPO concentration and the neutrophil count as determined by means of the blood cell counting apparatus is shown in FIG. 8(b).

Figure 8B:
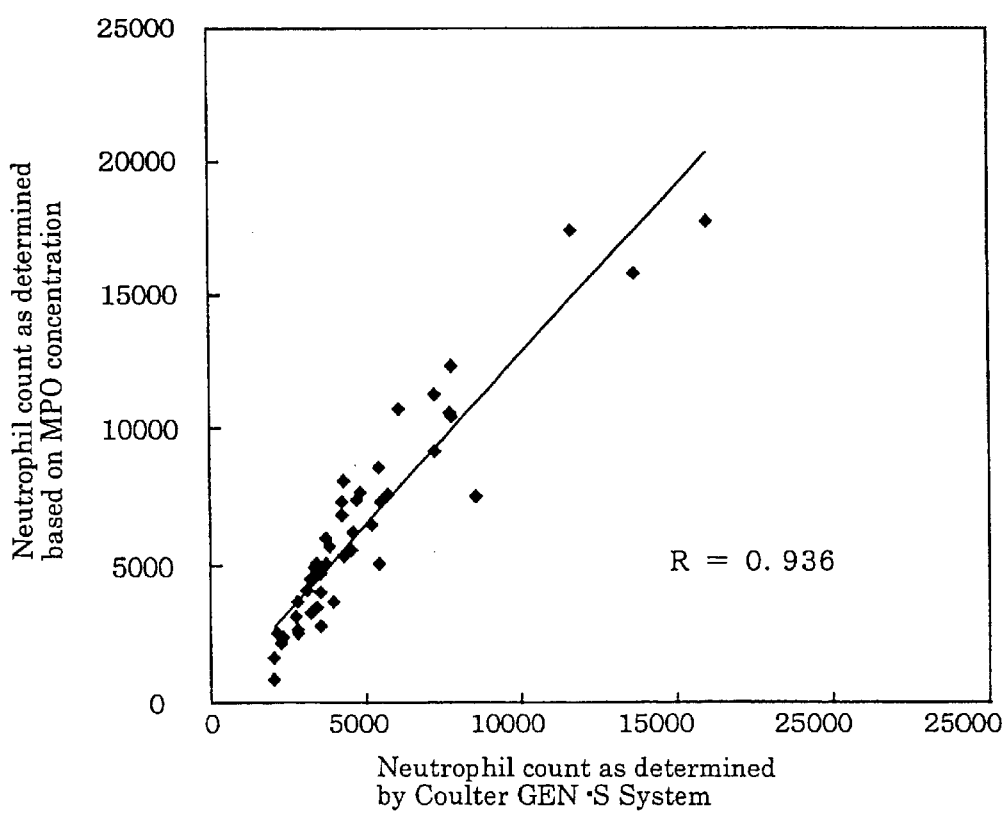
FIG. 8(b) is a diagram showing the correlation between the neutrophil counts as determined based on the MPO concentrations and the neutrophil counts as determined by a blood cell counting apparatus.

As apparent from FIG. 8(b), it was confirmed that, even in the case of the human whole blood samples including those having a white blood cell count of 10,000 cells/µl or more, there is a good correlation ($y=1.2542x+241.85$; $R=0.936$) between the neutrophil count as determined by the method of the present invention and the neutrophil count as determined by means of a blood cell counting apparatus. Therefore, by previously preparing a regression line showing the correlation between the MPO concentration and the neutrophil count in whole blood, a neutrophil count of a whole blood sample can be obtained simply by measuring the MPO concentration of the whole blood sample, wherein the obtained neutrophil count exhibits a good correlation with a neutrophil count as determined by means of a blood cell counting apparatus. Thus, by the method of the present invention, accurate determination of a neutrophil count of a whole blood sample can be easily performed, even in the case of the whole blood samples including those having a white blood cell count of 10,000 cells/µl or more.

EXAMPLE 11

Measurement of the MPO and CRP Concentrations in a Single Sample

To 10 ml of healthy human whole blood having a white blood cell count of 4,800 cells/µl was added 1 ml of an aqueous 11% (w/v) solution of Triton™ X-100 (manufactured and sold under the brand of SIGMA™, U.S.A.), and the resultant mixture was stirred well and then allowed to stand at room temperature for 60 minutes to thereby lyze the white blood cells to obtain a (whole blood sample/surfactant) mixture containing the lyzed white blood cells. The obtained mixture was designated as "Sample A". A portion of Sample A was taken out therefrom, and MPO (manufactured and sold by Elastin Products Co., INC., U.S.A.) and CRP (manufactured and sold by Oriental Yeast Industries, Co., Ltd., Japan) were added to the taken-out portion so that the final concentrations of the added MPO and CRP became 10 µg/ml and 2 µg/ml, respectively, thereby obtaining Sample B. Another portion of Sample A was taken out therefrom, and MPO and CRP were added to the taken-out portion so that the final concentrations of the added MPO and CRP became 20 µg/ml and 10 µg/ml, respectively, thereby obtaining Sample C. A still another portion of Sample A was taken out therefrom, and MPO and CRP were added to the taken-out portion so that the final concentrations of the added MPO and CRP became 30 µg/ml and 50 µg/ml, respectively, thereby obtaining Sample D.

There was provided a silicon wafer having its surface coated with a polysiloxane polymer (the silicon wafer is manufactured and sold by BioStar, U.S.A.), which silicon wafer is described in International Application Publication No. WO94/03774. The silicon wafer was immersed for 24 hours at 4° C. in a 10 µg/ml solution of a rabbit anti-human MPO antibody (manufactured and sold by Calbiochem-Novabiochem Corporation, U.S.A.) in 0.1 M HEPES (pH 8.0) or in a 10 µg/ml solution of a rabbit anti-human CRP antibody (manufactured and sold by Oriental Yeast Industries, Co., Ltd., Japan) in 0.1 M HEPES (pH 8.0), thereby causing the anti-MPO antibody or the anti-CRP antibody to be adsorbed on the surface of the silicon wafer coated with a polysiloxane. Then, the silicon wafer having the antibody adsorbed thereon was washed with water, and the water drops remaining on the wafer were removed using a nitrogen gas, followed by air drying.

The above-mentioned Samples A, B, C and D were individually diluted 100-fold with a 0.1 M HEPES (pH 8.0)

solution to obtain diluted solutions. 10 μl of each of the diluted solutions was taken and individually mixed with 30 μl of a solution of an HRP-labled anti-MPO antibody in an Eppendorf tube or with 30 μl of a solution of an HRP-labled anti-CRP antibody in an Eppendorf tube (wherein the HRP labeling of the antibody was performed in the same manner as in Example 2), and the resultant mixtures were individually subjected to a reaction for 10 minutes at room temperature.

30 μl of each of the resultant reaction mixtures was taken and put on the above-mentioned silicon wafer having the anti-MPO antibody or anti-CRP antibody adsorbed thereon, and the resultant was allowed to stand for 10 minutes at room temperature. Then, the thus treated silicon wafer was washed with water, and the water drops remaining on the wafer were removed using a nitrogen gas, followed by air drying. Immediately after the drying, 30 μl of TMB fast (manufactured and sold by Kirkegaad & Perry Laboratories, U.S.A.) was put on the silicon wafer and reacted for 5 minutes to thereby form a precipitation layer on the surface of the silicon wafer. After completion of the reaction, the silicon wafer was washed with water, and the water drops remaining on the wafer were removed using a nitrogen gas, followed by air drying, to thereby obtain a silicon wafer carrying a protein which had been bound to the antibody immobilized on the wafer and which had been visualized. The degree of the staining of the visualized protein was visually examined and given an evaluation symbol selected from the group consisting of "−", "±", "+", "++" and "+++", which are in the order of from the low degree of staining to the high degree of staining. The results are shown in Table 7.

TABLE 7

| Sample | Results of visual evaluation | |
|---|---|---|
| (100-fold dilution) | Detection of MPO | Detection of CRP |
| A | − | − |
| B | ± | + |
| C | + | ++ |
| D | ++ | +++ |

As apparent from Table 7, a sample obtained by treating a whole blood sample with a surfactant can be measured with respect to both MPO and CRP concentrations.

EXAMPLE 12

The silicon wafer obtained in Example 11, which had a precipitation layer formed thereon, was subjected to a measurement of the thickness of the precipitation layer by means of an ellipsometer in which polarizing plates are fixed (incident angle: 70°, angle of the polarizing plate on the side of incidence: 20°, angle of the polarizing plate on the side of detection: 10° He/Ne laser) (manufactured and sold by Sigma Koki Co., Ltd., Japan), thereby determining the amount of the protein in each of the samples. The measurement was conducted 10 times and a mean value was obtained. The results are shown in Table 8.

TABLE 8

| Sample | Results of detection using an ellipsometer (μW) | |
|---|---|---|
| (100-fold dilution) | Detection of MPO | Detection of CRP |
| A | 39.10 | 40.31 |
| B | 50.46 | 70.45 |
| C | 66.37 | 176.74 |
| D | 71.36 | 315.29 |

As apparent from Table 8, a sample obtained by treating a whole blood sample with a surfactant can be measured with respect to both MPO and CRP concentrations.

INDUSTRIAL APPLICABILITY

By the method of the present invention for determining a white blood cell count, the determination of a white blood cell count and/or a neutrophil count of a whole blood sample can be performed easily and rapidly without the need to separate blood cells from the whole blood sample. Further, by the determination method of the present invention, in addition to a white blood cell count of a whole blood sample, the concentration of C-reactive protein contained in the same whole blood sample can be measured. Therefore, by the method of the present invention, the presence or absence of an infectious disease and the graveness of an inflammation can be diagnosed rapidly and easily and at low cost.

What is claimed is:

1. A method for determining a white blood cell count of a whole blood sample, which comprises:
    (a) mixing a whole blood sample with a surfactant to thereby obtain a mixture;
    (b) allowing said mixture to stand for a time sufficient to lyze the white blood cells contained in said whole blood sample and release intrinsic myeloperoxidase from said white blood cells;
    (c) measuring the concentration of the released myeloperoxidase in said mixture; and
    (d) determining the white blood cell count in said whole blood sample, based on the concentration of said released myeloperoxidase.

2. The method according to claim 1, wherein, in step (c), the concentration of C-reactive protein contained in said whole blood sample is measured in addition to the concentration of said released myeloperoxidase.

3. The method according to claim 2, wherein, in step (c), both the concentration of said myeloperoxidase and the concentration of said C-reactive protein are measured by an immunological method.

4. The method according to claim 1, wherein, in step (c), the concentration of said released myeloperoxidase is measured by an immunological method.

5. The method according to claim 4, wherein said immunological method is an enzyme immunoassay.

6. The method according to claim 4, wherein said immunological method is an optical immunoassay.

7. The method according to claim 1, wherein said surfactant is a nonionic surfactant.

8. The method according to claim 7, wherein said nonionic surfactant has a hydrophile-lipophile balance (HLB) value of from 12 to 14.

9. The method according to claim 7, wherein said nonionic surfactant is a polyethylene oxide compound having a saturated or unsaturated hydrocarbon bonded thereto.

10. The method according to claim 9, wherein said nonionic surfactant is at least one nonionic surfactant selected from the group consisting of a nonionic surfactant having a polyoxyethylene alkylphenyl ether structure, a nonionic surfactant which is a polyethylene oxide compound having an unsaturated aliphatic hydrocarbon bonded thereto, and a nonionic surfactant having a polyoxyethylene alkyl ether structure.

11. The method according to claim 10, wherein said nonionic surfactant is at least one nonionic surfactant selected from the group consisting of Triton™ X-114, Triton™ X-100, Igepal™ CA630, Nissan Nonion NS-208.5, Nissan Dispanol TOC, Brij™ 97, and Brij™ 56.

12. The method according to claim 1, wherein said surfactant is at least one cationic surfactant selected from the group consisting of hexadecyltrimethylammonium bromide, hexadecyltrimethylammonium chloride, didecyldimethylammonium chloride, dodecyltrimethylammonium chloride, dodecyltrimethylammonium bromide, octadecyltrimethylammonium chloride, tetradecylammonium bromide, dodecylpyridinium chloride, hexadecylpyridinium chloride, hexadecylpyridinium bromide, 1-laurylpy-ridinium chloride, and tetradecyltrimethylammonium bromide.

13. The method according to claim 1, wherein said surfactant is mixed with said whole blood sample in an amount such that the concentration of said surfactant in said mixture is in the range of from 0.2 to 10% (w/v).

14. The method according to claim 1, wherein, in step (b), said mixture is allowed to stand for not more than 1 hour.

15. The method according to claim 1, wherein said white blood cell count is a neutrophil count.

* * * * *